(12) United States Patent
Honey et al.

(10) Patent No.: US 11,397,774 B2
(45) Date of Patent: Jul. 26, 2022

(54) SYSTEM AND METHOD FOR DIGITAL ENHANCEMENT OF HIPPOCAMPAL REPLAY

(71) Applicant: THE GOVERNING COUNCIL OF THE UNIVERSITY OF TORONTO, Toronto (CA)

(72) Inventors: Christopher Honey, Toronto (CA); Morgan Barense, Toronto (CA); Christopher Martin, Toronto (CA); Andrew Xia, Toronto (CA); Bryan Hong, Toronto (CA); Rachel Newsome, Bradford (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 0 days.

(21) Appl. No.: 17/291,653

(22) PCT Filed: Nov. 8, 2019

(86) PCT No.: PCT/CA2019/051595
§ 371 (c)(1),
(2) Date: May 6, 2021

(87) PCT Pub. No.: WO2020/093169
PCT Pub. Date: May 14, 2020

(65) Prior Publication Data
US 2021/0406315 A1     Dec. 30, 2021

Related U.S. Application Data

(60) Provisional application No. 62/792,082, filed on Jan. 14, 2019.

(30) Foreign Application Priority Data

Nov. 9, 2018 (GB) .................................. 1818322
Jan. 14, 2019 (CA) .............................. CA 3030000

(51) Int. Cl.
*G06F 16/00* (2019.01)
*G06F 16/9038* (2019.01)
(Continued)

(52) U.S. Cl.
CPC ...... *G06F 16/9038* (2019.01); *G06F 16/9035* (2019.01); *G06N 5/022* (2013.01);
(Continued)

(58) Field of Classification Search
CPC .................................................. G06F 16/9035
See application file for complete search history.

(56) References Cited

U.S. PATENT DOCUMENTS

| | | |
|---|---|---|
| 2007/0022112 A1 | 1/2007 | Asukai et al. |
| 2007/0043459 A1 | 2/2007 | Abbott et al. |
| 2008/0138783 A1 | 6/2008 | Karkanias et al. |
| 2020/0106973 A1* | 4/2020 | Zhang .................. H04N 5/3535 |

FOREIGN PATENT DOCUMENTS

WO     2009/117272 A2     9/2009

OTHER PUBLICATIONS

Hodges, Steve, et al., SenseCam: A wearable camera that stimulates andrehabilitates autobiographical memory, 2011.
(Continued)

*Primary Examiner* — Ajith Jacob
(74) *Attorney, Agent, or Firm* — Bhole IP Law

(57) ABSTRACT

There is provided a system, method, and computer program for digital enhancement of hippocampal replay. In an embodiment, the method includes: creating one or more digital memories, each digital memory created by: receiving a tag associated with the digital memory from a user; receiving a captured digital memory from the user; and associating one or more additional attributes with the digital memory; creating a replay session, the replay session comprising one or more digital memories, by: associating a target digital memory with the replay session; and associating one or more other digital memories with the replay session if such one or more other digital memories meet a measure of commonality with the target digital memory, the measure of commonality at least based on the additional attributes; and displaying the replay session to the user within a predetermined period.

30 Claims, 19 Drawing Sheets

(51) Int. Cl.
*G16H 20/70* (2018.01)
*G06F 16/9035* (2019.01)
*G06N 5/02* (2006.01)
*G16H 40/67* (2018.01)
*G16H 50/20* (2018.01)
*G06V 40/16* (2022.01)
*G06V 20/00* (2022.01)

(52) U.S. Cl.
CPC ............ *G16H 20/70* (2018.01); *G06V 20/00* (2022.01); *G06V 40/172* (2022.01); *G16H 40/67* (2018.01); *G16H 50/20* (2018.01)

(56) References Cited

OTHER PUBLICATIONS

Alzheimer's Awareness Month: Introducing the Hippocamera, dated, Jan. 2017, retrieved from: https://www.cabhi.com/news/alzheimers-awareness-month-introducing-the-hippocamera/ on Jan. 3, 2019.
Overturning the Modular View of Memory in the Brain, Aiding, Alzheimer's Patients, dated Jan. 24, 2018 and retrieved from, https://www.cogneurosociety.org/overttuning-modular-view-memory-brain-aiding-alzheimers-patients/ on Jan. 3, 2019.
United Kingdom, Combined Search and Examination Report, GB1818322.8 dated Jan. 8, 2019.
International Search Report and Written Opinion, PCT/CA2019/051595, dated Feb. 26, 2020.

* cited by examiner

User-specified inputs 310

| Raw video 311 | Compressed video 312 |
|---|---|

| Audio tag 313 |
|---|

| Significance rating 314 |
|---|

System-specified inputs 320

| Date and time stamp 321 |
|---|
| Location (GPS) 322 |
| Background color 323 |
| Icon 324 |
| Replay information 325 |

Machine learning output 330

| Face recognition 331 |
|---|
| Scene recognition 332 |
| Object recognition 333 |

FIG. 3

SYSTEM AND METHOD FOR DIGITAL ENHANCEMENT OF HIPPOCAMPAL REPLAY

TECHNICAL FIELD

The following relates generally to assistive technology for cognition; and more particularly, to systems and methods for digital enhancement of hippocampal replay.

BACKGROUND OF THE INVENTION

Memory loss is the most common and debilitating cognitive impairment resulting from Alzheimer's disease (AD) and from the mild cognitive impairment (MCI) which often precedes AD. Memory loss diminishes one's sense of identity and autonomy, leading to a vicious cycle of social isolation and depression, which in turn exacerbates memory loss. Digital Memory Augmentation (DMA) generally involves portable devices to capture information about everyday episodes, allowing for later review and recollection. However, there can be various challenges and implementation problems with conventional DMA approaches.

SUMMARY OF THE INVENTION

There is provided a computer-implemented method for digital enhancement of hippocampal replay, the method comprising: creating one or more digital memories, each digital memory created by: receiving a tag associated with the digital memory from a user; receiving a captured digital memory from the user; and associating one or more additional attributes with the digital memory; creating a replay session, the replay session comprising one or more digital memories, by: associating a target digital memory with the replay session; and associating one or more other digital memories with the replay session if such one or more other digital memories meet a measure of commonality with the target digital memory, the measure of commonality at least based on the additional attributes; and displaying the replay session to the user within a predetermined period.

In a particular case, the predetermined period comprises a time delay after capturing of the digital memory.

In another case, the predetermined period is at least four hours.

In yet another case, the predetermined period comprises a window of time prior to when the user is expected or predicted to go to sleep on the day the digital memory was captured.

In yet another case, the window of time is less than or equal to two hours in duration.

In yet another case, creating the one or more digital memories further comprises: generating an associative representation with the digital memory, the associative representation comprising at least one of a background colour and a symbol; and displaying the associative representation when the respective digital memory is displayed.

In yet another case, the tag comprises at least one of a recorded audio, a recorded video, and inputted text.

In yet another case, the captured digital memory comprises at least one of video, an image, audio, and text.

In yet another case, the additional attributes comprise at least one of a date, a time stamp, location coordinates, replay information, a face recognition score, and an object recognition score.

In yet another case, the additional attributes comprise at least one of raw video attributes, compressed video attributes, audio tag attributes, and significance rating attributes.

In yet another case, the additional attributes comprise at least one of date and time stamp attributes, GPS co-ordinates attributes, background colour attributes, icon attributes, and replay information attributes.

In yet another case, the creating one or more digital memories further comprises assigning a numerical significance rating to each digital memory, the significance rating being classified as a high significance to denote relative importance and a low significance to denote relative unimportance.

In yet another case, the method further comprising associating each created digital memory with a queue associated with one of a plurality of bins, and wherein associating the target digital memory with the replay session further comprises selecting a digital memory from a top of the queue from a selected bin.

In yet another case, each bin has an associated age and importance, and wherein each digital memory is associated with a respective bin based on the age and importance associated with the digital memory.

In yet another case, selecting the digital memory from the top of the queue from the selected bin comprises: selecting the digital memory from a first bin associated with a relatively newer age and higher importance; if no digital memory that has not been displayed is present in the queue associated with the first bin, selecting the digital memory from a second bin associated with a relatively newer age and lower importance; if no digital memory is present that has not been displayed in the queue associated with the second bin, selecting the digital memory from a third bin associated with a relatively older age and higher importance; and if no digital memory is present that has not been displayed in the queue associated with the third bin, selecting the digital memory from a fourth bin associated with a relatively older age and lower importance.

In yet another case, the captured digital memory comprises a sequence of digital memories associated with a spatial location, and wherein the replay session comprises the sequence of digital memories displayed in sequence.

In another aspect, there is provided a system for digital enhancement of hippocampal replay, the system comprising one or more processors and a data storage device, the one or more processors configured to execute: a memory creation module to create one or more digital memories, each digital memory created by: receiving a tag associated with the digital memory from a user; receiving a captured digital memory from the user; and associating one or more additional attributes with the digital memory; a replay session module to create a replay session, the replay session comprising one or more digital memories, by: associating a target digital memory with the replay session; and associating one or more other digital memories with the replay session if such one or more other digital memories meet a measure of commonality with the target digital memory, the measure of commonality at least based on the additional attributes; and a display module to display the replay session to the user within a predetermined period.

In a particular case, the predetermined period comprises a time delay after capturing of the digital memory.

In another case, the predetermined period is at least four hours.

In yet another case, the predetermined period comprises a window of time prior to when the user is expected or predicted to go to sleep on the day the digital memory was captured.

In yet another case, the window of time is less than or equal to two hours in duration.

In yet another case, creating the one or more digital memories further comprises: generating an associative representation with the digital memory, the associative representation comprising at least one of a background colour and a symbol; and displaying the associative representation when the respective digital memory is displayed.

In yet another case, the additional attributes comprise at least one of a date, a time stamp, location coordinates, replay information, a face recognition score, and an object recognition score.

In yet another case, the additional attributes comprise at least one of raw video attributes, compressed video attributes, audio tag attributes, and significance rating attributes.

In yet another case, the additional attributes comprise at least one of date and time stamp attributes, GPS co-ordinates attributes, background colour attributes, icon attributes, and replay information attributes.

In yet another case, the creating one or more digital memories further comprises assigning a numerical significance rating to each digital memory, the significance rating being classified as a high significance to denote relative importance and a low significance to denote relative unimportance.

In yet another case, the memory creation module further associating each created digital memory with a queue associated with one of a plurality of bins, and wherein associating the target digital memory with the replay session further comprises selecting a digital memory from a top of the queue from a selected bin.

In yet another case, each bin has an associated age and importance, and wherein each digital memory is associated with a respective bin based on the age and importance associated with the digital memory.

In yet another case, selecting the digital memory from the top of the queue from the selected bin comprises: selecting the digital memory from a first bin associated with a relatively newer age and higher importance; if no digital memory that has not been displayed is present in the queue associated with the first bin, selecting the digital memory from a second bin associated with a relatively newer age and lower importance; if no digital memory is present that has not been displayed in the queue associated with the second bin, selecting the digital memory from a third bin associated with a relatively older age and higher importance; and if no digital memory is present that has not been displayed in the queue associated with the third bin, selecting the digital memory from a fourth bin associated with a relatively older age and lower importance.

These and other aspects are contemplated and described herein. It will be appreciated that the foregoing summary sets out representative aspects of the system and method to assist skilled readers in understanding the following detailed description.

BRIEF DESCRIPTION OF THE DRAWINGS

A greater understanding of the embodiments will be had with reference to the figures, in which:

FIG. 3 illustrates an exemplary block diagram of digital memory;

DETAILED DESCRIPTION OF VARIOUS EMBODIMENTS OF THE INVENTION

Figure 1:
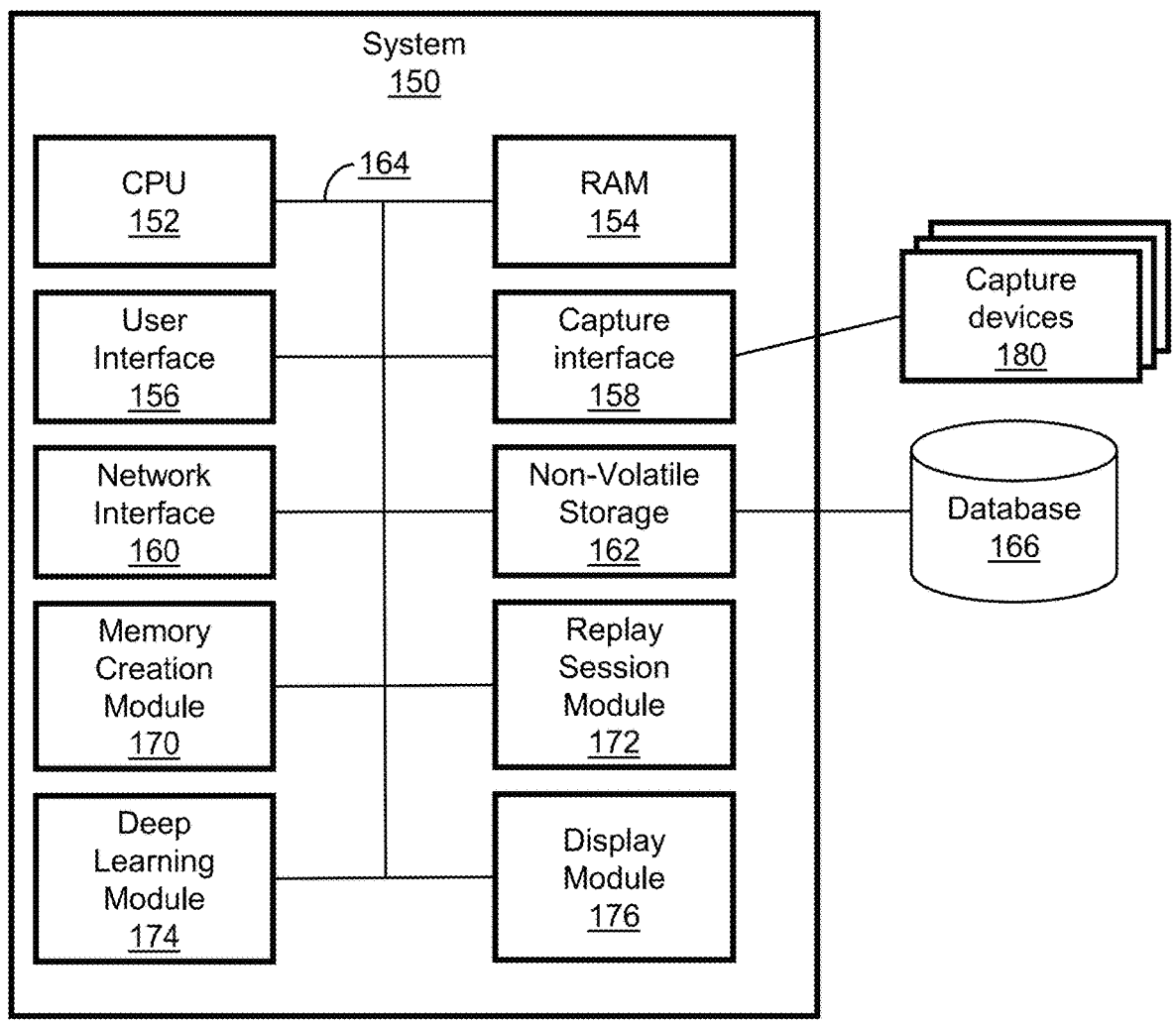
FIG. 1 illustrates a block diagram of a system for digital enhancement of hippocampal replay, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures, and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine, or device exemplified herein that executes instructions may include or otherwise have access to computer-readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer-readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information, and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application, or module herein described may be implemented using computer readable/executable instructions that may be stored or otherwise held by such computer-readable media and executed by the one or more processors.

Various approaches to Digital Memory Augmentation (DMA) typically focus on development of wearable hardware (for example, cameras) that are capable of automatically capturing photographs, audio, and video from daily life. In other words, they provide an emphasis on life-logging through the creation of digital memories, which from the perspective of the neurobiologically-mediated memory system can be analogous to encoding an event memory. Within this context, automated picture or video capture may be typically controlled by a user-defined schedule (for example, photographs taken at 30 second intervals), that can be flexibly supplemented by sensors that detect environmental state changes (for example, a change in ambient sound or luminance).

Typically, as a consequence of pursuing smaller, more discrete hardware, some DMA devices require that content comprising digital memories be transferred from the wearable camera to either a computer or smartphone. Across platforms, this is most commonly accomplished using wired, Wi-Fi, or Bluetooth connectivity. Platform-specific software can then be used to manually curate and organize digital memories on the computer or smartphone. The user can then review the content within the management software at their discretion. From the perspective of a neurobiologically-mediated memory system, this review can be analogous to replaying and/or retrieving a previously encoded event memory.

In these approaches, replay is typically unprompted, unstructured, and not distributed over time. Typically, digital memories can be reviewed only after they have been transferred to either a computer or smartphone. Accordingly, whether content is reviewed at all can depend critically on the user remembering to do so. Moreover, the user's motivation may depend on their ability to export photos and video onto an alternative device and their ability to easily use platform-specific software. Commonly, content may be reviewed in a single session at the end of each day. Furthermore, in some approaches, digital memories are often lacking richness (for example, merely still photographs) and/or contextual information that may be otherwise difficult to recall in memory-impaired populations; and thus, may not be conducive to later recall. In this way, such approaches may not be guided by advances in the cognitive neuroscience of memory in any systematic way.

In some cases, research has demonstrated that massed learning is considerably less effective than distributed learning. During review/replay, some DMA devices do not present digital memories in a manner that is generally conducive to later recall. In the human brain, long-term consolidation of memories is thought to be supported by replay. In particular, a brain region known as the hippocampus is believed to rapidly store memory patterns, and then uses these to "replay" the experience for the rest of the brain, thus strengthening and inter-connecting the memory traces in other regions. Critically, events are replayed by the hippocampus much more rapidly than they originally occurred, grouped based on spatio-temporal context, and replay can be both forward as well as backward (i.e., events within an episode can be played in reverse).

In embodiments described herein, there is provided a recall routine that is individualized to a user. In the present embodiments, advantageously, digital memories can be selected using machine learning methodologies and dynamic similarity estimations. In some embodiments, replay sessions can be structured around content that comprises a single digital memory, initially selected based on rules that prioritize recently created, highly significant content. Although the initial selection protocol can use rules that are common across individuals, in some cases, these rules can interact with input that is unique to each user (for example, significance ratings). In a particular case, subsequent digital memories comprising a given replay session can be selected based on an adaptive machine-learning approach that optimizes long-term memory consolidation. In some embodiments, machine learning approaches can be used to quantify similarities between the digital memory initially selected for replay and one or more other previously recorded events. Similarity estimates can be predicated on, for example, spatio-temporal proximity, face recognition, object recognition, scene recognition, and the like. In some cases, similarity estimates are dynamically updated as new digital memories are created, meaning that replay routines can be continually evolving toward increasingly optimized replay. In this way, some of the present embodiments can tailor replay at the level of individual users as well as the level of individual replay sessions.

Advantageously, the present embodiments can determine patterns that are generally not determinable by the user and, based on such patterns, can intelligently adapt recall and replay. Cognitive psychology generally holds that a person's conscious perception and subsequent memory is fundamentally linked to attention. Sensory systems generally have capacity limits at the level of conscious perception, meaning that the majority of stimuli a person encounters in daily life can go unnoticed. Specifically, the phenomenon of inattentional blindness describes the fact that people are often unable to perceive a stimulus that is in plain sight, in particular when the stimuli are complex and dynamic (for example, videos). Accordingly, a human observer is likely to be effectively 'blind' to many aspects of a digital memory (for example, video). This is particularly important given that the extent to which any two events are meaningfully related is determined by, for example, the complex co-occurrence of people, objects, scenes, time, and space. By using machine learning approaches, which are generally not subject to attentional constraints, the present embodiments allow for identification of patterns of co-occurrence that are highly likely to go unnoticed to a human observer. Advantageously, the present embodiments can optimize replay using available information associated with a digital memory, rather than merely a subset of information that is consciously perceived by a user. Additionally, the present embodiments can identify meaningful connections that are highly likely to goes unnoticed by a user. For example, this can be reflected in behaviour that benefits from prior exposure in the absence of declarative knowledge regarding an explicit awareness of prior patterns of co-occurrence. The probabilistic learning of the present embodiments can occur outside of conscious awareness of the user, and, in some cases, can use computational mechanisms similar to that of the human hippocampus. Specifically, prior research in patient populations has revealed that individuals with compromised hippocampal integrity/functioning have significant impairments in their ability to learn based on statistical regularities across multiple stimuli regardless of their complexity. Generally, neurologically and cognitively healthy individuals are able to identify some regularities across multiple complex stimuli, but are generally unable to consciously characterize these regularities in a manner that can be effectively brought to bear on manual optimization of replay routines. In contrast, some of the present embodiments can advantageously enable the identification of meaningful connections across many episodes, through the use of adaptive statistical learning, supported by machine learning.

In the present embodiments, there is provided a system, method and computer program for digital enhancement of hippocampal replay. In this sense, digital enhancement of hippocampal replay presents a digital technique for augmenting memory strengthening. In an embodiment, the system can capture auditory and visual data from real-life episodes for the user and subsequently replay these episodes to the user, at an advantageous time. Advantageously, memory traces can be strengthened via replay from an external device, in addition to the replay that is produced internally via the hippocampus. Especially in individuals with memory impairments, in whom the structures supporting hippocampal replay may be compromised, the externally mediated replay may produce substantial memory benefits.

In one aspect, embodiments disclosed herein can provide digital enhancement of hippocampal replay which is prompted and structured by a system, rather than by the user, and may occur throughout the day, as it does for hippocampal replay. Prompts to create memory recordings may also be automated. These intelligent automations can be beneficial because they minimize demands on prospective memory and ensure that memory capture and replay are spaced throughout the day, providing a connected and coherent trace of daily episodes.

In another aspect, embodiments disclosed herein can provide digital enhancement of hippocampal replay which mimics the behaviours of the hippocampus. The system may select the information to be replayed, and the nature of the replays (for example, frequency, duration, speed, forward/backward structure, contextual framing, spatial proximity to other episodes, temporal order in relation to other episodes, and time of day of replay) to optimally match parameters of hippocampal replay and with broader considerations of memory function (for example, interference). For example, events could be replayed by the hippocampus much more rapidly than they originally occurred, and replay can be both forward as well as backward (i.e., events within an episode can be played in reverse).

In another aspect, embodiments disclosed herein can provide digital enhancement of hippocampal replay that provides contextual replay.

The following embodiments generally provide technological solutions to the technical problems related to enhancing hippocampal operation through implementation of digital memory augmentation (DMA). In an embodiment, a DMA system can be used to improve memory for personally experienced events for users in either healthy, at-risk, or memory-impaired populations. In an embodiment, the system can be used to create event-specific digital memories from real-life episodes by capturing videos of notable events and replaying these catalogued videos to the user according to a score, for example, by importance. The DMA system can enhance hippocampal operation by using a structure and timing of replay in view of principles of cognitive psychology and cognitive neuroscience. In an embodiment, the system can be used to provide predetermined reminders to a user to view previously recorded events at a number of times throughout their day, in a sped-up manner, to optimize memory recall for the video. In this way, advantageously, the system can enhance cognitive memory with its corresponding neurobiological underpinnings.

Turning to FIG. 1, a system for digital enhancement of hippocampal replay 150 is shown, according to an embodiment. In this embodiment, the system 150 is run on a client-side device (for example, a smartphone or tablet). In further embodiments, the system 150 can be run on any other computing device; for example, a desktop computer, a laptop computer, a server, a smartwatch, or the like.

In some embodiments, the components of the system 150 are stored by and executed on a single computing system. In other embodiments, the components of the system 150 are distributed among two or more computer systems that may be locally or remotely distributed.

FIG. 1 shows various physical and logical components of an embodiment of the system 150. As shown, the system 150 has a number of physical and logical components, including a central processing unit ("CPU") 152 (comprising one or more processors), random access memory ("RAM") 154, a user interface 156, a capture interface 158, a network interface 160, non-volatile storage 162, and a local bus 164 enabling CPU 152 to communicate with the other components. CPU 152 executes an operating system, and various modules, as described below in greater detail. RAM 154 provides relatively responsive volatile storage to CPU 152. The user interface 156 enables an administrator or user to provide input via an input device, for example a mouse or a touchscreen. The user interface 156 can also output information to output devices, such as a display or speakers. In some cases, the user interface 156 can have the input device and the output device be the same device (for example, via a touchscreen). The capture interface 158 communicates with one or more capture devices 180 to capture a 'digital memory.' The one or more capture devices 180 can be, for example, a video capture device, an audio capture device, or the like. In further embodiments, the capture interface 158 can retrieve already captured digital memories from the local database 166 or a remote database via the network interface 160. 'Digital memory', as used herein, is understood to mean a recording of still image, video, audio, or any of these, of a set length representative of an event occurring to a user. The contents of such digital memory are described in greater detail herein.

The network interface 160 permits communication with other systems, such as other computing devices and servers remotely located from the system 150, such as for a typical cloud-based access model. Non-volatile storage 162 stores the operating system and programs, including computer-executable instructions for implementing the operating system and modules, as well as any data used by these services. Additional stored data, as described below, can be stored in a database 116. During operation of the system 150, the operating system, the modules, and the related data may be retrieved from the non-volatile storage 162 and placed in RAM 154 to facilitate execution.

In an embodiment, the system 150 further includes a number of conceptual modules to be executed on the one or more processors 152, including a memory creation module 170, a replay session module 172, a machine learning module 174, and a display module 176.

Figure 2:
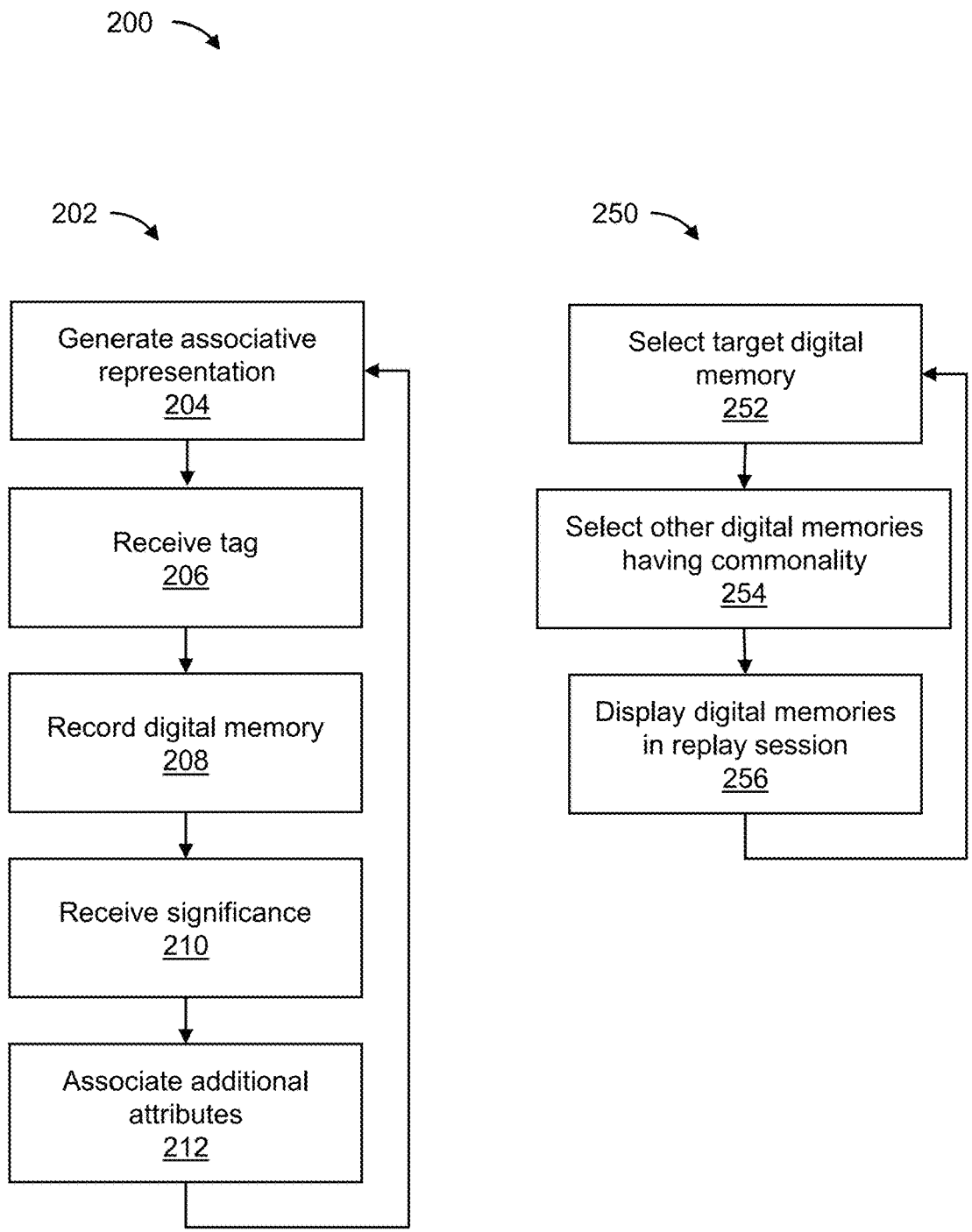
FIG. 2 illustrates a flow diagram of a method for digital enhancement of hippocampal replay, according to an embodiment.

FIG. 2 illustrates a method 200 for digital enhancement of hippocampal replay, in accordance with an embodiment. As part of the method 200, a digital memory can be created by the memory creation module 170 via a digital hippocampal memory creation 202, and a replay session of one or more digital hippocampal memories can be created and presented by the replay session module 172 via a digital hippocampal memory replay 250.

In the digital hippocampal memory creation 202, at block 204, the memory creation module 170 generates an associative representation with a subject digital memory. In a particular case, the associative representation can include a unique background color. In another case, the associative representation can include a unique symbol alone, or in combination with the unique background color. The symbol can be, for example, a silhouetted object.

At block 206, a tag is received from a user by the memory creation module 170, via the user interface 156 or the capture interface 158, that captures a general overview or gist of an event captured by the subject digital memory. The tag can be, for example, recorded audio, recorded video, inputted text, or the like. In a particular case, the recorded audio or video is time-limited (for example, 8 seconds), or the inputted text is character-limited (for example, 150 characters).

At block 208, the memory creation module 170 receives the subject digital memory captured with one or more capture devices 180 by the user. While the present embodiment describes the digital memory as a video, any other suitable type of captured media is contemplated; for example, image, audio, descriptive text, or the like. In a particular case, the captured digital memory is time-limited (for example, 24 seconds).

At block 210, the memory creation module 170 receives a significance rating from the user via the user interface 156. The significance rating associated with the subject digital memory to denote the relative importance of the associated event. In an example, the significance rating can be on a score of one to five, with five being the most important.

At block 212, in some cases, the memory creation module 170 can associate one or more additional attributes with the digital memory. In an example, the additional attributes can be one or more of a date and time stamp, location coordinates, replay information, a face recognition score, a scene recognition score, and an object recognition score.

Blocks 202 to 212 can be repeated by the memory creation module 170 for creating each subsequent digital memory.

In the digital hippocampal memory replay 250, at block 252, the replay session module 172 selects an initial target digital memory, having predetermined attribute properties, as described herein, for a subject replay session. At block 254, in some cases, the replay session module 172 selects one or more other digital memories having a commonality with the target digital memory for the subject replay session, as described herein. In some cases, the commonality is based on the additional attributes associated with each digital memory.

At block 256, the display module 176 displays each of the digital memories in the subject replay session to the user. In some cases, the digital memory is displayed for a limited time (for example, 24 seconds). In some cases, the digital memory is displayed sped-up (for example, a 24-second recording is sped up to 8-seconds in length). In some cases, prior to, during, or after each respective replay session, the display module 176 displays the respective associative representation to the user. The associative representation can be displayed prior to, or after, the digital memory in a separately displayed screen. The associative representation can be displayed during the digital memory as overtop of, or beside, the display of the digital memory.

Blocks 252 to 256 can be repeated by the system 350 for displaying subsequent replay sessions.

Referring now to FIG. 3, an exemplary conceptual block diagram of the contents of digital memory 300, in accordance with an embodiment, is shown. In an embodiment, each conceptual digital memory is associated with an 'event' and includes a plurality of attributes, with corresponding values for the respective digital memory. In an embodiment, each attribute can be included in one or more of i) user-specified input 310 attributes, ii) system-specified input 320 attributes, or iii) input from machine-learning algorithm 330 attributes.

In an embodiment, the user-specified input 310 attributes can include raw video 311 attributes, compressed video 312 attributes, audio tag 313 attributes and significance rating 314 attributes. The raw video 311 attributes can include one or more raw video files associated with the respective digital memory; for example, a 24-second raw video. The compressed video 312 attributes can include one or more compressed video files, compressed from the raw video files, associated with the respective digital memory; for example, compressed to eight-seconds. In further embodiments, the compression factor can be more or less than a factor of three. In some cases, audio can be stripped from the compressed videos. The audio tag 313 attributes can include audio recordings associated with a high-level summary of the event. Each audio tag 313 can be combined with an associated compressed video. In a particular case, the audio tag 313 can have approximately the same length as the associated compressed video; for example, also having a length of eight-seconds. The significance rating 314 attributes can include a user-supplied rating, or an automatically-generated rating, associated with the event. In an exemplary case, the rating can be on a numerical scale, for example, from 1 to 5 with 5 being the most significant event and 1 being the least significant event.

In an example, video processing can be initiated immediately after creation of the digital memory. In this example, a 24-second raw video 311 is temporally compressed by a factor of three, yielding an 8-second sped-up compressed video 312. Although, in some cases such a compression factor may be less than has been observed in physical hippocampal replay in a rodent brain, the present inventors have experimentally determined, via using different compression factors and video lengths, that further compression can be disorienting for human users. In some cases, audio can be removed from the compressed video to allow an audio tag, as described herein, to be played concurrently with the video during replay.

In an embodiment, the system-specified input 320 attributes associated with each respective digital memory can include date and time stamp 321 attributes, GPS co-ordinates 322 attributes, background colour 323 attributes, icon 324 attributes, and replay information 325 attributes. In an example, the replay information 325 attributes can include a log of memory-specific replay statistics, including count, date, and time of all replays of the digital memory.

In an embodiment, the machine-learning input 330 attributes can include face recognition 331 attributes, scene recognition 332 attributes, and object recognition 333 attributes.

Any suitable machine learning model, methodology, tool, or paradigm can be used for object recognition. In an example, the MobileNet neural network model, accessible via the Object Detection API built into TensorFlow, can be used. This object and face detection model is optimized for low latency and efficient performance on mobile devices. In most cases, such models are advantageous when (i) they provide access to a large number (>50) of object categories along with their spatial locations in the image; and (ii) they provide detailed (e.g. vectorial) representations of faces and objects, so that the presence of exact matches (e.g. the same person) can be identified across videos. In most cases, these items of information are sufficient for extracting basic event information and measuring event similarity. Further extensions based on dynamics of the video are also possible.

Figure 4:
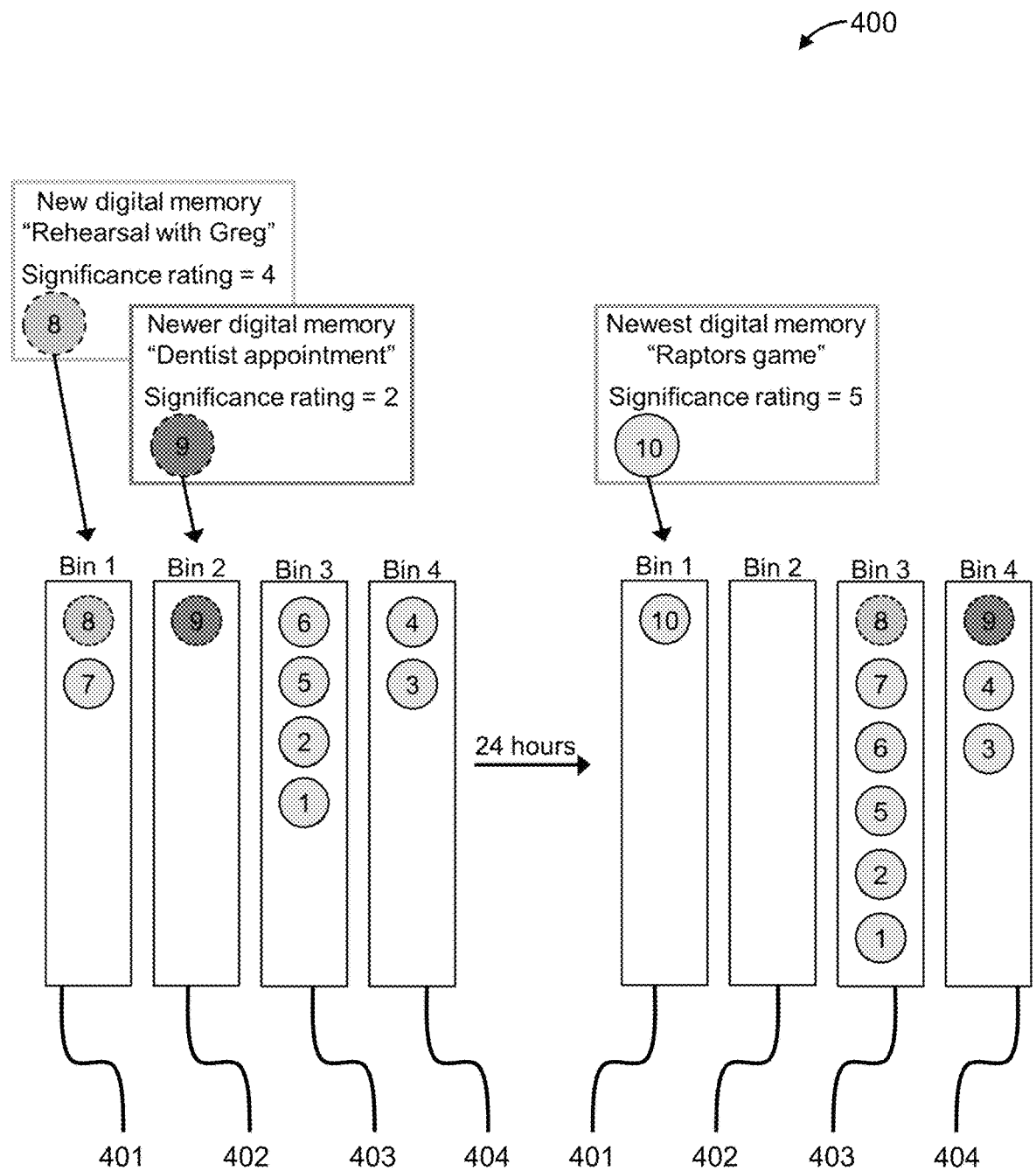
FIG. 4 illustrates a block diagram of an exemplary digital memory storage architecture, in accordance with the system of FIG. 1.

Referring now to FIG. 4, a block diagram of an exemplary digital memory storage architecture 400 is shown. In this embodiment, each of the digital memories can be stored in one of a plurality of conceptual 'bins'; in a particular example, in one of four such bins. While four bins are illustrated in this example, any suitable number of bins, each having certain attributes associated therewith, are contemplated. In some cases, bin indexing can be dynamically updated in a memory-specific manner; for example, after 24 hours, memories can "migrate" from bins 1 and 2 to bins 3 and 4, respectively. In a particular case, each bin can have an associated age and importance; where digital memories are sorted by bin according to their age and importance.

In this example, bin 1 401 can be associated with new memories (for example, those less than 24 hours old) that have high significance ratings (for example, a score of between 3 to 5); bin 2 402 can be associated with new memories that have low significance ratings (for example, a score of between 1 to 3); bin 3 403 can be associated with old memories (for example, those greater than 24 hours old) that have high significance ratings (for example, a score of between 3 to 5); and bin 4 404 can be associated with old memories (for example, those greater than 24 hours old) that have low significance ratings (for example, a score of between 1 to 3).

In the example shown in FIG. 4, a new digital memory "(8) Rehearsal with Greg" is created, and the user associates via input using the user interface 156 a significance rating of 4 (a high significance rating). This digital memory can then be added to the top of the queue of bin 1 401. Another new digital memory "(9) Dentist appointment" is created, and the user associates via input a significance rating of 2 (a low significance rating). That digital memory is added to the top of the queue of bin 2 402. After a 24 hour period, the digital memories in bin 1 401 are moved to the top of the queue of bin 3 403. Additionally, the digital memories in bin 2 402 are moved to the top of the queue of bin 4 404. After the 24 hour period, a new digital memory "(10) Raptors game" is created, and the user associates via input a significance rating of 5 (a high significance rating). This digital memory is added to the top of the queue of bin 1 401.

In this example, digital memories can be 'queued' within each bin, such that new memories can be added to a top of the queue for replay selection of the digital memories in such bin. In this example, after a digital memory is replayed, it can be moved to a bottom of the queue of the respective bin. The textual labels used in FIG. 4, such as "(8) Rehearsal with Greg", are for the reader's reference. They may, for example, depict the content of the digital memory or an audio tag associated with the digital memory (e.g., a video). In the case of an audio tag that is associated with a video, the audio tag can be replayed at the time of a video replay session.

Figure 5:
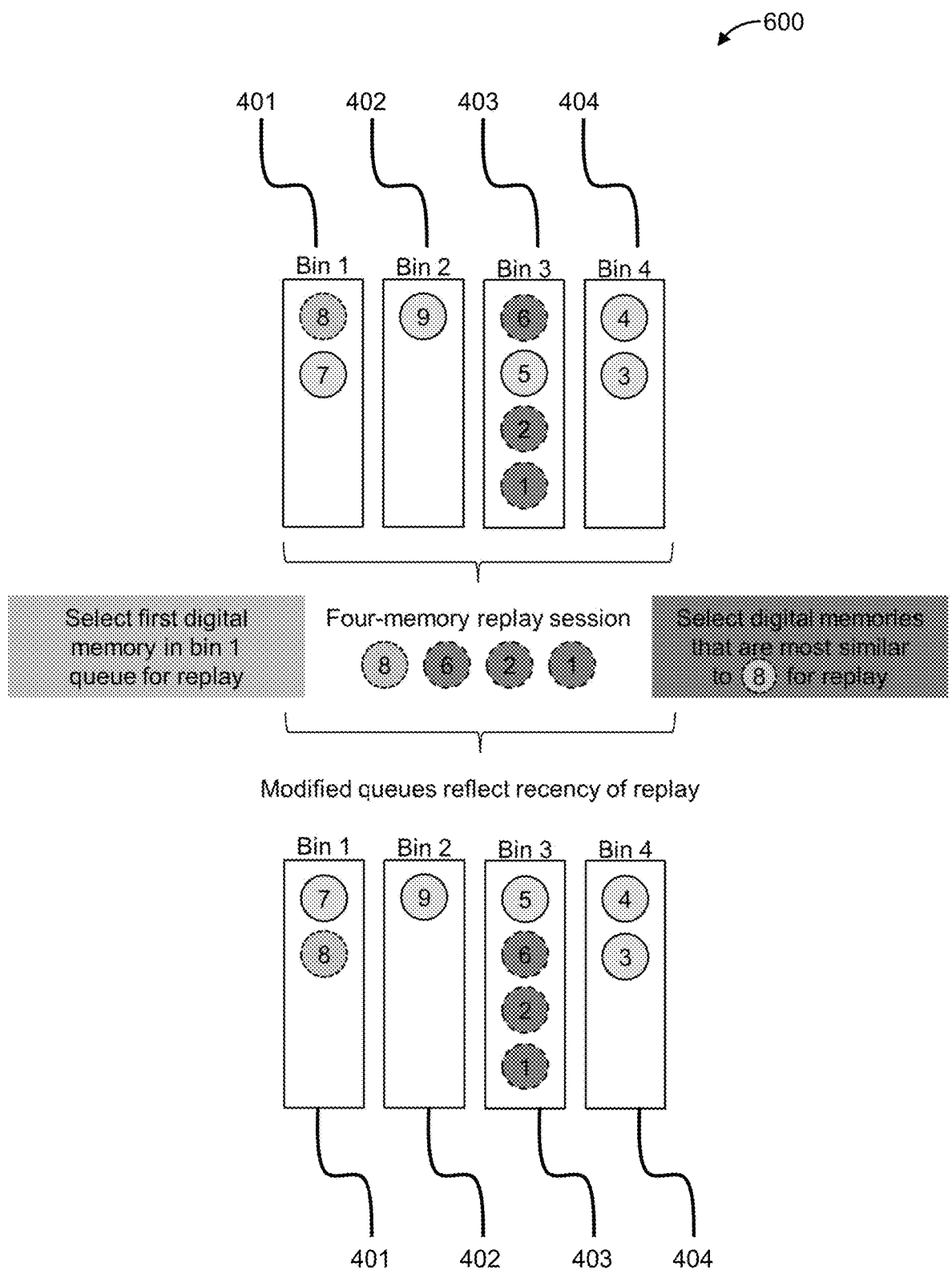
FIG. 5 illustrates a block diagram of another exemplary digital memory storage architecture, in accordance with the system of FIG. 1.

Referring now to FIG. 5, a block diagram of an exemplary digital memory replay architecture 600, using the bins of FIG. 4, is shown. In some cases, not all digital memories need be presented during a replay session consisting of one or more digital memories. Rather, each replay session can include replay of a subset of the digital memories; for example, up to a maximum of five digital memories. In an example, replay sessions can be structured around selection criteria that emphasize same-day replay of content embedded within a situationally aware context. This selection criteria can be determined by the replay session module 172 by anchoring a recently created digital memory in the queue of bin 1 401. In this example, the replay session can be anchored by memory 8. Then, digital memories that are most similar to the anchored digital memory selected from bin 1 401 can be selected to be added to the replay session. In this example, the digital memories added are digital memory 6, digital memory 2, and digital memory 1. After the digital memories have been selected for the replay session, the queues within each bin can be modified to reflect recency of replay. In this example, digital memory 8 is shuffled to the bottom of bin 1 401; digital memory 6, digital memory 2, and digital memory 1 are moved to the bottom of the queue associated with bin 3 403.

An intended substantial advantage of the present embodiments is the ability for the system 350 to intelligently and automatically curate digital memories based on user-recorded content. In this way, the present embodiments are able to cluster digital memories at the time of replay in a manner that advantageously align with neurocognitive principles associated with the user. For example, in a healthy brain, memories are typically coherently organized: one memory leads to another related memory. Therefore, the system 350 advantageously simulates hippocampal replay, and thus can boost memory for single events, by reinforcing relationships between meaningfully connected memories.

For example, on the basis of commonalities at the level of people and the nature of the event.

In an embodiment, the technical problem of determining the above commonalities can be overcome, for example, using machine vision technology by the machine learning module 174 that enables automated detection of various aspects of the digital memories (for example, facial identity, locations, and settings). In some embodiments, machine vision techniques for facial and scene categorization can be used by the machine learning module 174 in order to cluster digital memories, such that the digital memories in the same cluster can be meaningfully connected. In some cases, training of the machine vision models by the machine learning module 174 can take place on remote computing devices. The training data can include databases of labeled images (for example, in some cases, hundreds of thousands of such labelled images). In a particular case, the machine vision models can comprise separate models, at least one of a model for detecting each of faces, objects, and scene recognition. Once the face, object, and scene recognition models are trained by the machine learning module 174, they can be packaged into a reduced form that can be efficiently deployed on a user's device, for example a smartphone.

In the present embodiments, the machine learning models may be machine vision models or other suitable classification approaches. In a particular example of other approaches, the machine vision technology can rely on the "random forest" model for image classification. Any suitable machine learning model that can obtain labels for the videos can be used.

In some cases, training of the machine learning models can include comparing specific entities in one device-recorded scene (for example, a specific person, John, at a restaurant) against specific entities in other scenes (for example, John in the living room at home).

In some cases, the face, object, and scene recognition models can be separate models; in other cases, the face, object, and scene recognition can be the same model (or otherwise combined). Some machine vision techniques can recognize faces as well as objects, and output both parameters simultaneously. Outputs of faces, scenes and objects can later be combined to determine event similarity. In some cases, the object recognition models may look for objects; for example, tables, chairs, knives, forks, windows, bottles, cats, dogs, or the like. In some cases, the scene recognition models can look for scenes; for example, indoors or outdoors classification, restaurant, sports field, bedroom, office, church, or the like. In an example embodiment, the recognition models can be deployed on mobile using the Tensor Flow. In an exemplary embodiment, machine vision technology deployed may be used that is appropriate for mobile devices (for example, MobileNet version 1 or 2).

Using the determinations of the machine vision models by the machine learning module 174, the replay session module 172 can determine a similarity between any two events based on a comparison of values in at least one of people, scene, and object attributes. In some cases, the comparison can also include a comparison of GPS coordinates associated with a place each digital memory was captured in order to determine nearness in geographical space. Thus, the replay session module 172 can determine that two distinct digital memories have the highest commonality score if they have a measure of commonality in at least one of persons, scenes, objects, and locations. Conversely, the replay session module 172 can determine that two memories have the lowest similarity if they have a low measure of commonality for at least one of different scenes, persons, objects, and locations. Advantageously, replay sessions of a plurality of digital memories can include a plurality of recorded events that are linked, for example, not only by when the original memory occurred, but also by other aspects such as who was there and what was happening. In some cases, such clustering of digital memories can be continuously updated as new digital memories are added; thus, the clustering can become increasingly more refined with each addition. In an example, face recognition can include executing OpenCV Face Detect and OpenCV Face Recog libraries. In an example, object detection can include executing an Android-Object-Detection library. In an example, MobileNet version 1 can be implemented via TensorFlow. In an example, if compressed vector representations of all of the videos are extracted using machine vision tools, then the replay session module 172 can efficiently compare all digital memories.

Referring now to FIGS. 6A-6D, an example of digital memory clustering based on machine learning techniques and location acquisition is illustrated. As discussed with respect to FIG. 5, the replay session module 172 selects digital memories for a replay session that have a commonality score that is closest to the digital memory at the top of the queue in bin 1. In order to determine a similarity between a target digital memory (the digital memory at the top of the queue in bin 1) and other digital memories in storage, a commonality score can be assigned to each of the other digital memories and the target digital memory. In some cases, the commonality scores can be a weighted average of the component scores for each pair, the component scores being a measure of commonality for at least one of people, scene, objects, and location attributes.

Figure 6A:
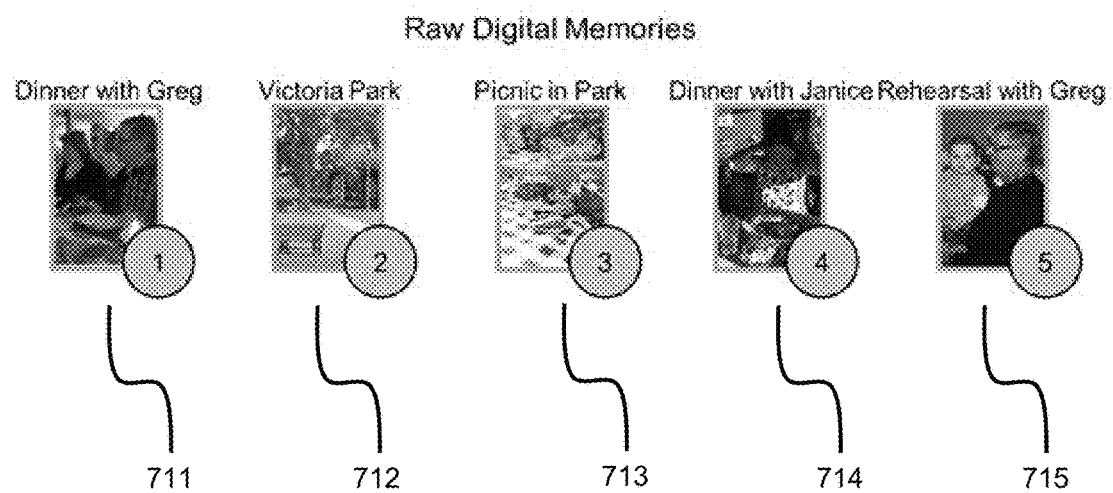
FIG. 6A illustrates screenshots of exemplary digital memories, in accordance with the system of FIG. 1.

FIG. 6A illustrates still frames exemplifying five possible raw digital memories in storage. In a particular case, these still frames are representative of videos taken of an event. The five events include: "(1) Dinner with Greg" as digital memory 1 711, "(2) Victoria Park" as digital memory 2 712, "(3) Picnic in Park" as digital memory 3 713, "(4) Dinner with Janice" as digital memory 4 714, and "(5) Rehearsal with Greg" as digital memory 5 715.

Figure 6B:
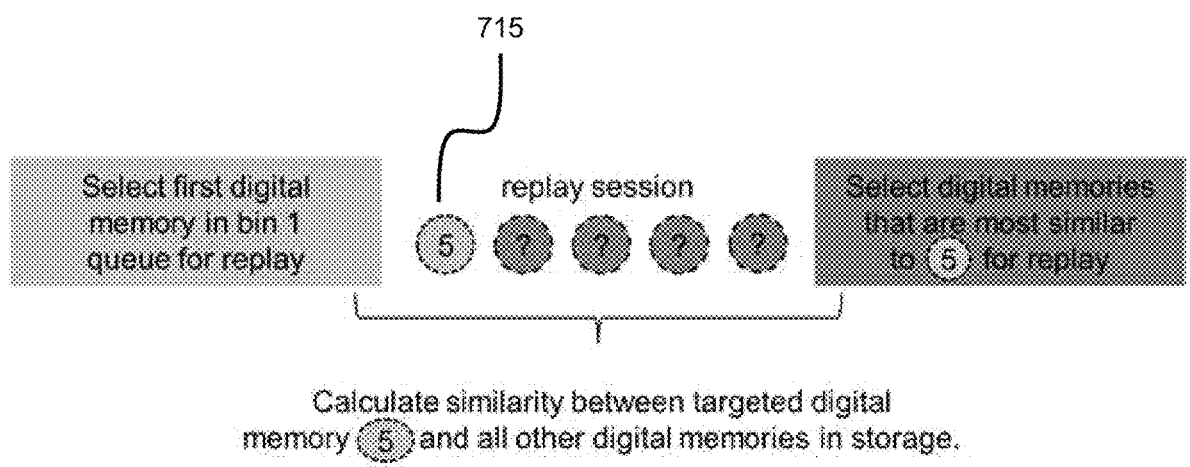
FIG. 6B illustrates a block diagram of a state of a replay session in the example of FIG. 6A, in accordance with the system of FIG. 1.

FIG. 6B illustrates a block diagram of a state of a replay session after a first digital memory has been selected for replay. In this example, the first digital memory selected for replay is digital memory 5 715 as it is the digital memory that is highest in a queue associated with bin 1. In this example, the system 350 can select up to four additional digital memories (shown as circles with question marks therein) for inclusion in a replay session. The additional digital memories to be selected are those determined to be most similar to digital memory 5 715.

Figures 6C, 6D:
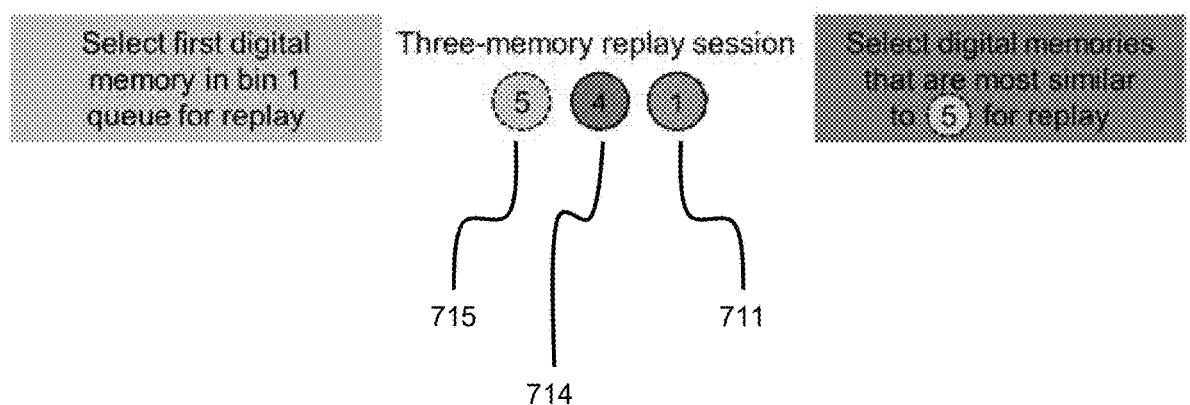
FIG. 6C illustrates a table listing component attribute scores for the digital memories in the example of FIG. 6A, in accordance with the system of FIG. 1.
FIG. 6D illustrates a subsequent block diagram of a state of a replay session in the example of FIG. 6A, in accordance with the system of FIG. 1.

FIG. 6C illustrates a table listing component attribute scores for each digital memory. The percentages in the table reflect the degree of contribution of a particular attribute to the digital memory. To the right of that table, there is shown a column of commonality scores for the other digital memories with digital memory 5 715. In that column, the system 350 determines a commonality score for pair (5,1) to be 0.68, for pair (5,2) to be 0.04, for pair (5,3) to be 0.09, for pair (5,4) to be 0.56, and for pair (5,5) to be 1. In this example, relatively high commonality scores for pairs (5,1) and (5,4) are due to similarities in people and scene attributes.

In a particular case, the machine vision models can output percentages of the scene (for example, "55% confidence this is Greg"). In other cases, where the model does not output percentages, the vector of outputs can be converted to a percentage by a divisive normalization operation. The commonality scores may be determined by the machine learning module 174 based on initial weights for the different attributes being updated through interaction with the user. In some cases, in the GPS column, Lat # and Long # (e.g., Lat1 and Long1) can be used to depict the spatial coordinates associated with the recorded event (latitude and longitude).

FIG. 6D illustrates a block diagram for a state of the replay session after the additional digital memories for replay have been selected. In this example, due to the relatively high commonality scores, a second digital memory selected for replay is digital memory 4 714 and a third digital memory selected for replay is digital memory 1 711.

Figure 7:
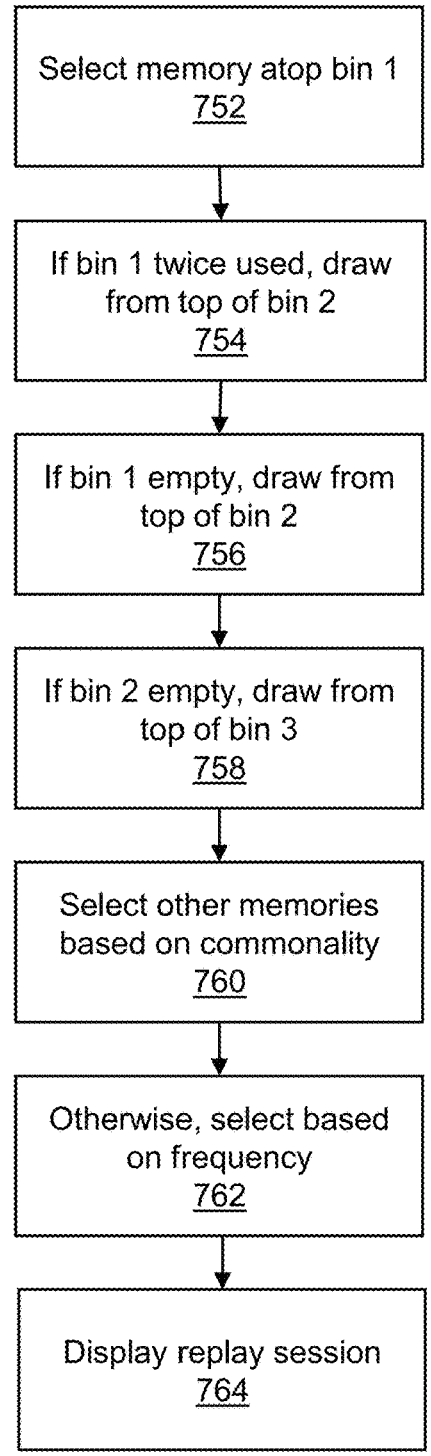
FIG. 7 illustrates a flow diagram of a method for replay session digital memory selection, according to the method of FIG. 2.

The system 350 advantageously simulates hippocampal replay and optimizes memory performance by promoting same-day replays that are embedded within a situationally aware context. In some cases, much of the replay behavior can be determined by initial selection determinations. In an example, FIG. 7 illustrates a method for replay session digital memory selection 750 to select an initial target digital memory and additional digital memories, in accordance with the embodiments described herein. At block 752, an initial selection is made to select a digital memory that is atop a queue associated with bin 1.

In an embodiment, the system 350 can use a rule to prioritize replay of recently recorded, highly significant memories (i.e., bin 1). In this embodiment, initial selection queries bin 1 first. In this way, an initial memory is drawn from the top of the bin 1 queue (i.e., the most recently recorded memory that has been fully processed). Subsequently, the memory is sent to the bottom of the bin 1 queue. In some cases, there may be exceptions to initial selection from bin 1. For example, if i) there are no memories in bin 1, or ii) if all memories in bin 1 have already been replayed twice within the last 24 hours. In this example, in these cases, the initial selection queries memories in bin 2 (i.e., recently recorded, low significance memories), with initial selection drawn from the top of the queue of bin 2. At block 754, in an embodiment, if the digital memories in the queue of bin 1 have already been included in two replay sessions during the preceding 24 hours, then the next initial selection will be drawn from bin 2. In this case, the digital memory drawn from bin 2 will be selected from the top of a queue associated with bin 2, after rank ordering by replay frequency (i.e., the memory replayed least frequently). In some cases, if newly created memories are subsequently added to bin 1, subsequent selections will be drawn from bin 1.

At block 756, in some cases, if no recently created digital memories were rated as being highly significant, then the queue of bin 1 will be empty. In this case, the system 350 can select a digital memory from the top of a queue associated with bin 2. Significance ratings of 3, 4, or 5 are considered to denote highly significant events. Ratings of 1 or 2 are considered to reflect low significance. At block 758, if no new memories have been created for at least a day, then in some cases, the queues of bin 1 and bin 2 may be empty. In this case, the system 350 can select the digital memory at the top of the queue in bin 3. Selecting from bin 3 reflects the prioritization of high significance remote events over low significance remote events.

In this embodiment, the order of bin queries is bin 1 then bin 2. The order of the queue in bins 1 and 2 is determined by recency of recording and recency of replay. In this embodiment, newly recorded memories are added to the top of the queue. As memories from the top of the queue are replayed they get shuffled to the bottom of the queue, thus moving older memories or previously replayed memories to the top of the queue. In some cases, there may be exceptions. For example, if the bin 2 query has been invoked and i) there are no memories in bin 2, or ii) if all memories in bin 2 have already been replayed twice within the last 24 hours. In an example, in these cases, then the initial selection queries memories in bin 3 (i.e., remote, high significance memories), with initial selection drawn from the top of the queue. The queue order in bin 3 (as well as bin 4) can be determined by frequency of replay. For example, memories can be sorted in ascending order by frequency of replay. Thus, in this example, remote memories that have been replayed least often are at the top, whereas those that have been replayed most often are at the bottom. It is contemplated that other initializations or order of bin queues can be used. At block 760, regardless of which bin the initial target digital memory was selected from, the system 350 selects other digital memories for the replay session that are contextually similar to the target digital memory based on commonality score. In most cases, the other digital memories are selected regardless of which bin they are assigned.

At block 762, in some cases, in the event that there are no other digital memories that have a commonality score with the initial target digital memory above a predetermined threshold, or there are very few other digital memories with low commonality scores (e.g., all scores less than 0.1), selection of "related" memories can be based on replay frequencies rather than similarity. In this way, the system 350 can select digital memories from the bottom of rank-ordering of digital memories in the queues of bins 3 and 4 (thus, ranking based on replay frequency). In other words, the digital memories that have been approximately replayed the least frequently will be selected.

At block 764, the system 350 displays the replay session with the selected digital memories for the user.

In embodiments of the present disclosure, the method for replay session digital memory selection 750 can advantageously make use of bin attributes that relate to event recency and user provided significance ratings. Generally, the recency attribute 24 hours ago or >24 hours ago) can be predicated on empirical research that indicates hippocampal replay privileges recent events over more remote events. Moreover, replaying more recent events enables their consolidation while the details of the memory are still available. Replaying memories after they have been degraded (due to decay or interference) would lower the upper limit on the richness and detail available in the consolidated memory. In this way, storing recent and remote memories in different bins, as described herein, advantageously enables prioritization of newer content.

In some embodiments, the significance attribute (high or low) can be predicated on user feedback. In some cases, for reasons that vary both across and within individuals, users may occasionally record content that has little personal significance. In this way, users may grow tired due to replaying too many insignificant memories at the expense of more meaningful memories. Advantageously, storing high and low significance memories in different bins, as described in some of the present embodiments, enables prioritization of important content.

Selection rules related to the above attributes can advantageously balance the optimization of memory performance (i.e., promotion of recent content) with user experience (i.e., promotion of significant content). In an embodiment, a first-order selection rule prioritizes recent events over remote events (bins 1 and 2 over bins 3 and 4). A second-order (i.e., subsidiary) selection rule prioritizes high significance over low significance (bin 1 over bin 2, and bin 3 over bin 4).

In some cases, the system 350 can determine a replay session schedule and display notifications to the user based on such schedule. In some cases, the replay session schedule and notifications can be based on the digital memory selection approach described herein. As described, the selection approach can optimize mnemonic benefit through situating recently created content into a situationally aware context that is defined by relationships with older memories. In some cases, it has been determined to be optimally beneficial to display the digital memories within a day of their creation; and in some cases, within several hours of their creation (for example, within 3 hours of their creation). In such a case, the system 350 can create a replay schedule such that each digital memory is prompted to be replayed within, for example, 3 hours of its creation. With such prompt, the user is displayed a notification (sounds and/or visual) that serve to remind the user to initiate a replay session within 3 hours of the most recent recording of a digital memory. In some cases, subsequent replay reminders can be issued by the system 350 at regular intervals; for example, every 3 hours. In some cases, the replay schedule may be altered by the user.

Advantageously, the replay schedule, in conjunction with the embodiments described herein with respect to digital memory creation and replay selection, can optimize the benefits of replay sessions. The notifications can take any suitable form; for example, a system-wide notification that can include a gentle chime, vibration, and/or text-based message that is temporarily visible on screen, even waking a device up if it is in sleep mode.

In some embodiments, the system 350 provides replay within a predetermined number of hours to optimize memory consolidation. In these embodiments, the system 350 privileges recent events over more distant events. In this way, replaying more recent events enables their consolidation while the details of the memory are still available. Replaying memories after they have been degraded (due to decay or interference) may lower the upper limit on the richness and detail available in the consolidated memory. In some cases, notifications can also be issued to the user if such user has not created any new digital memories within a certain timeframe; for example, within 24 hours. In some cases, these types of notifications can be beneficial to counter potential prospective memory problems (i.e., failure to remember to do something) in users with memory impairment.

Figure 8:
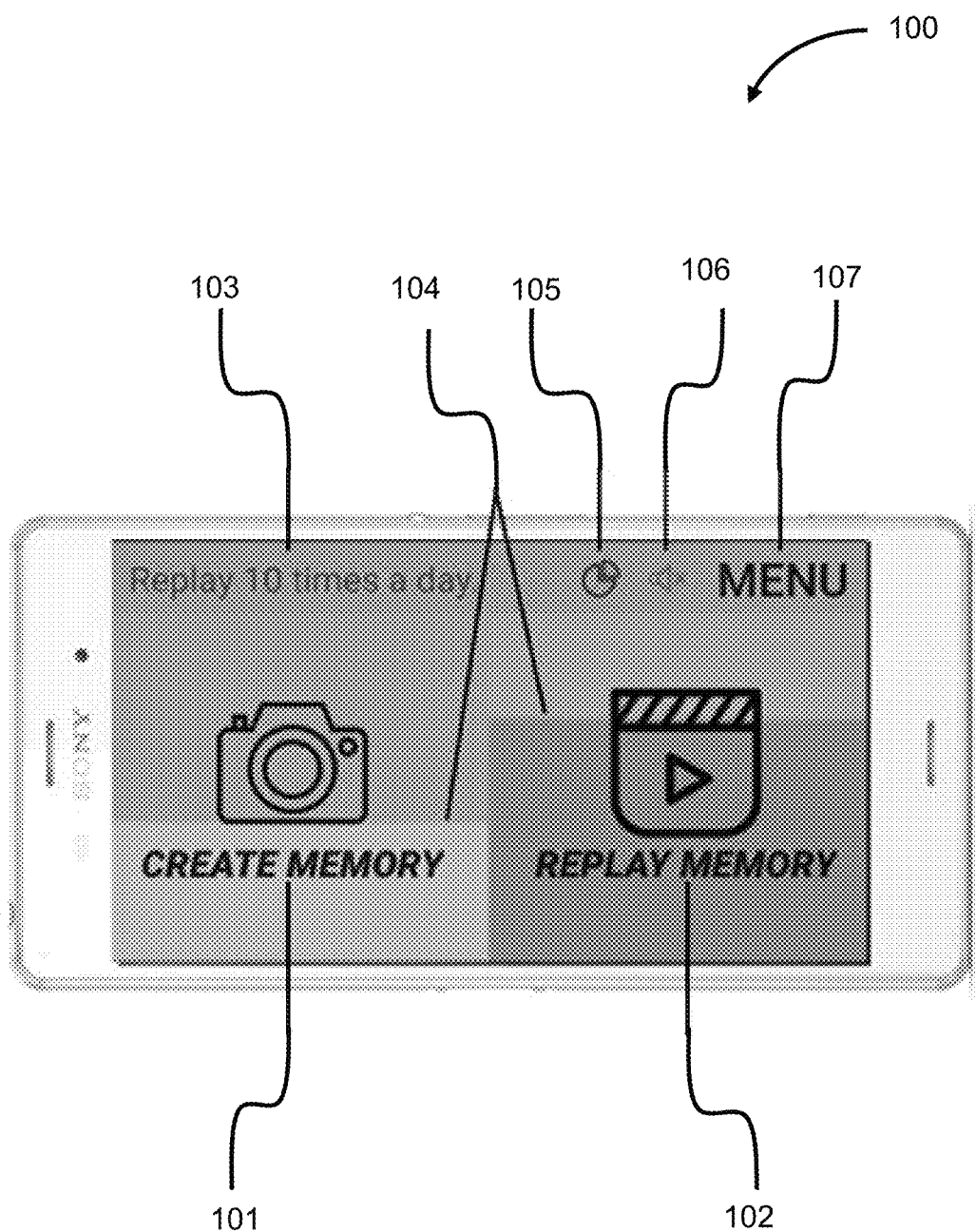
FIG. 8 illustrates an example of a home screen, in accordance with the system of FIG. 1.

Referring now to FIG. 8, an example of a home screen 100, as displayed by the display module 176 via the user interface 156, is shown. While a specific arrangement is exemplified for the purpose of illustration, any representation of the systems and methods described herein can be used. This exemplary home screen 100 is advantageously intuitive to ensure that a user is able to easily access the functions of the system 150; for example, creation of digital memories and replay of digital memories. In this exemplary home screen 100, a create memory button 101 can be located on a left side of the home screen 100 and can be color-coded to ensure that it remains distinct from other features. In this example, a touch of the create memory button 101 can initiate recording for creation of a digital memory as described herein. Also in this exemplary home screen 100, a replay memory button 102 can be located on a right side of the home screen and can be color-coded to ensure that it remains distinct from the other features. In this example, a touch of the replay memory button 102 can initiate a replay session.

Also in this exemplary home screen 100, a text element 103 (for example, a text crawl) in a top-left corner can provide evidence-based suggestions that can optimize mnemonic benefit. In some cases, these suggestions can reflect results from empirical research and user feedback. The following are examples of such suggestions:

Example 1—"Be sure to space your replay sessions throughout the day". This suggestion is based on the well-established finding that distributed learning produces better memory outcomes than does massed learning sessions.

Example 2—"Make your audio tags as distinctive and unique as possible". This suggestion is based on evidence indicating that distinctive cues promote better recollection than do generic cues. That is to say, "Eating dinner with Jim and Carol at the bistro after a round of golf", will evoke more detailed retrieval than will "Eating dinner".

Example 3—"Remember to charge your phone each night". This suggestion reflects feedback from older adult participants who had no previous experience using a cell phone. Also in this exemplary home screen 100, a usage indicator 104 can be provided; in this example, to both the digital memory creation side and the replay session side of the home screen 100. In this way, users can easily estimate how many digital memories they have created and replayed in a given day based on changes in size and/or coloration on the left and right side of the screen, respectively. For example, each time the user creates a digital memory, a lighter shade of orange can incrementally progress from the bottom to the top of the left side of the screen. In conjunction, each time the user watches a replay session, a darker shade of blue can incrementally progress from the bottom to the top of the right side of the screen.

Also in this exemplary home screen 100, a usage indicator 105 can allow users to view a number or symbol representing the number of digital memories that have been created and/or replayed. In this example, the user can press the usage indicator 105, which can then display a chart or table with a summary of user activity. Also in this exemplary home screen 100, a notification toggle 106 can allow the user to activate, deactivate, or select notifications. Also in this exemplary home screen 100, a menu button 107 can allow the user further customization; for example, customization of sounds, notification style, or the like, via a control or settings dialogue.

Figure 9:
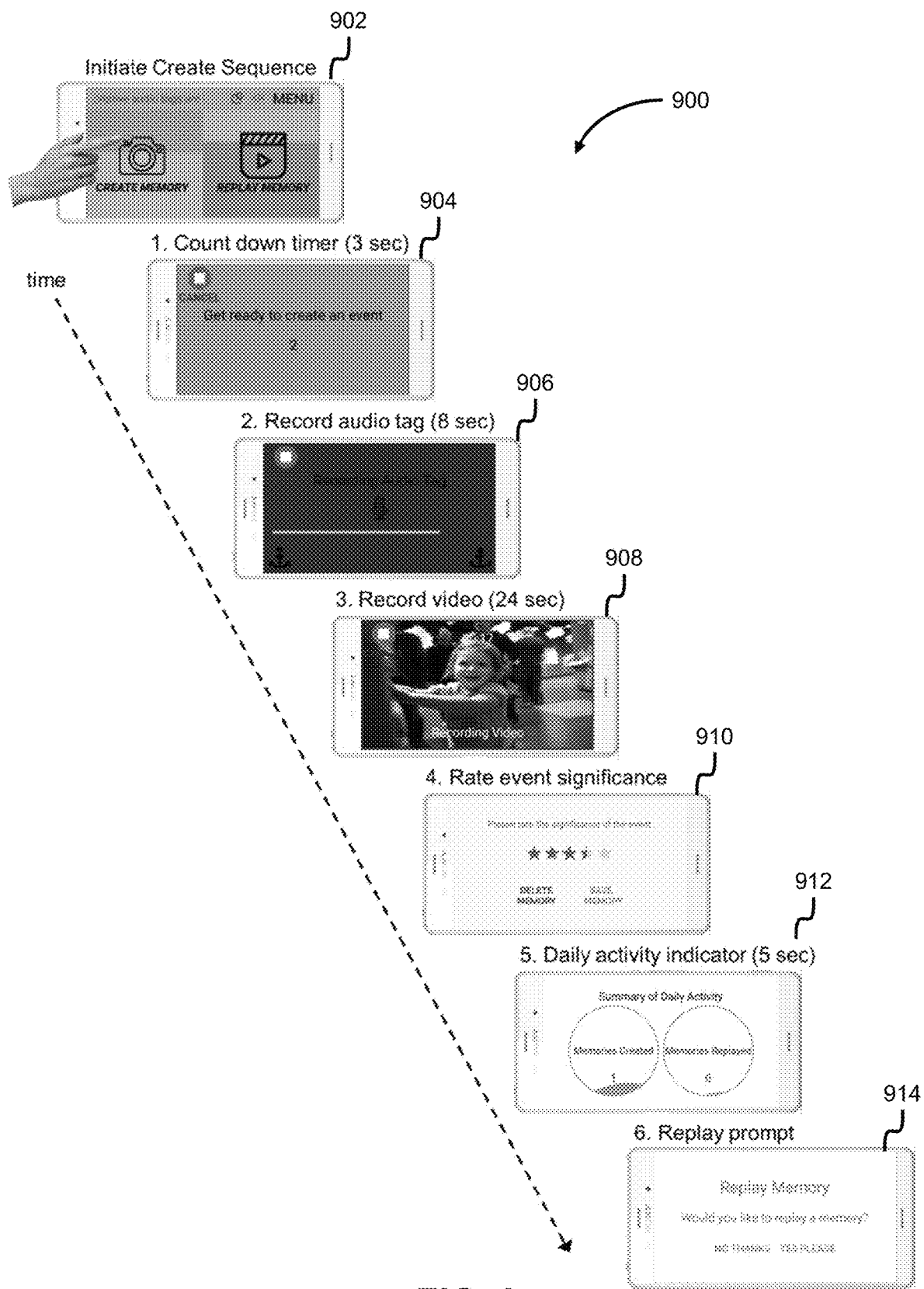
FIG. 9 illustrates an example of a screen progression for creation of a digital memory, in accordance with the system of FIG. 1.

Referring now to FIG. 9, an example of a screen progression 900 for creation of a digital memory, as displayed by the display module 176 via the user interface 156, in accordance with the system 150, is shown. While a specific screen progression is exemplified for the purpose of illustration, any screen progression and arrangement using the systems and methods described herein can be used. At a first screen 902, the create memory button 101 is selected by a user.

At a second screen 904, a countdown timer is displayed to the user; in this example, a 3-second countdown timer. In this example, during this time, a screen background color can be randomly generated, and in some case, a silhouette icon can also be randomly selected to be shown (for example, from a set of 10 silhouette icons). In some cases, these silhouette icons can also be displayed on bottom left and right corners of the screen. In this example, advantageously, this background color-silhouette icon pairing can be associated with the recorded digital memory and shown again at the time of replay of the digital memory to help disambiguate digital memories that have overlapping content. In this example, a 'cancel' button appears on the screen. Selecting the cancel button at any point throughout the digital memory creation process can be used to launch a dialogue in which the user will have the option to (i) recreate the memory or (ii) return to the home screen.

In this example, the background and silhouette can provide a salient and distinctive cue that aids in disambiguating events with high overlap (e.g., similar audio tag, similar location, and/or similar people). This aspect of the design can thus parallel the phenomenon of hippocampal pattern separation, whereby memory traces corresponding to highly similar events are represented in distinct neural codes. In this way, the interfering effect of related memories is minimized. Advantageously, displaying the background and silhouette prior to recording the video can establish and reinforce the relationship between the to-be-recorded event and the distinctive background/icon. At a third screen 906, in some cases, a user can record an audio tag as part of or associated with a digital memory; in this example, an 8-second audio tag. The audio tag is intended to capture a gist of the event; for example, "having fish and chips with John and Mary at Olde York." In this example, during the audio tag recording, a timer bar can be displayed to the user, moving from right to left, to indicate an amount of time that has elapsed. The present inventors have determined through empirical research, together with user feedback, that around 8 seconds is optimal for older adults (aged 60-80 years) to record personally meaningful audio tags that are sufficiently distinct for disambiguation of related events. However, other lengths of audio tags can be used.

At a fourth screen 908, the capture interface 158 captures an event occurring to the user as a digital memory; in this example, a 24-second video is captured. In this example, a countdown timer is displayed to the user together with text indicating that a digital memory (or video) is currently being recorded. The present inventors have determined through empirical research, together with user feedback, that around 24 seconds is the shortest duration that is i) sufficient to capture critical aspects the event, and ii) is evenly divisible by the length of the audio tag (i.e., 8 seconds). However, other lengths of digital memories can be used.

At a fifth screen 910, in some cases, a user can rate a significance of the event; in this example, on a 5-point star-rating scale. In some cases, at this screen the user can also be presented with the option of saving the digital memory or discarding it. In this case, the significance rating can be used to denote a relative importance of the event. Whereby, highly rated events are those that the user wishes to replay more frequently (e.g., visit with grandchildren). These values can be used by the system 350 for the purpose of structuring replay sessions, as described herein.

At a sixth screen 912, in some cases, the user can be presented with feedback indicating that number of digital memories created and replayed during a current day or time-period. In an example, the displayed counters can be reset to zero each day at a specific time; for example, at 4:00 am.

At a seventh screen 914, in some cases, a user can be presented with an option to launch a replay session, as described herein. In some cases, based on the user's device, this replay session may not include the digital memory that had just been created due to processing demands.

Figure 10:
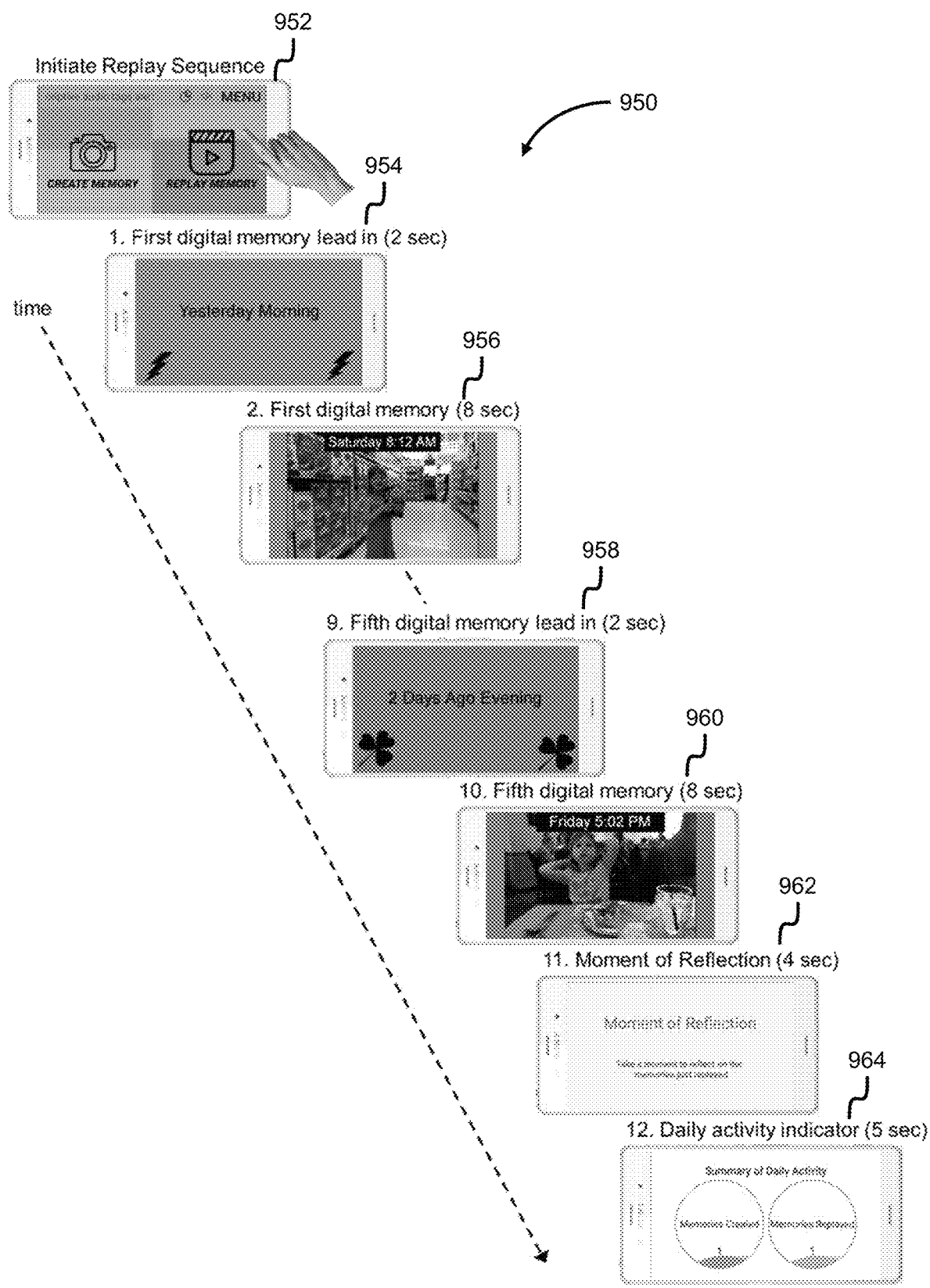
FIG. 10 illustrates an example of a screen progression for display of a replay session, in accordance with the system of FIG. 1.

Referring now to FIG. 10, an example of a screen progression 950 for display of a replay session, as displayed by the display module 176 via the user interface 156, in accordance with the system 150, is shown. While a specific screen progression is exemplified for the purpose of illustration, any screen progression and arrangement using the systems and methods described herein can be used. At a first screen 952, the replay memory button 102 is selected by a user.

At a second screen 954, in some cases, a lead-in screen can be displayed to show an approximate time and date of a first digital memory to be displayed in accordance with the embodiments described herein; for example, the approximate time and date can be "Yesterday Morning". Concurrently, the memory-unique background colour and icon (in this example, presented in the bottom left and right corner) associated with the digital memory can also be displayed. In this example, the lead-in screen can be displayed for a period of two seconds; however, other time-periods are possible.

At a third screen 956, the first digital memory is displayed to the user. In this example, the associated audio tag and video are played concurrently. In this example, a time and date stamp associated with the recording of the digital memory can be overlaid at the top of the screen (for example, "Saturday 8:12 AM"). The system 350 then progresses through each digital memory, selected by the system 350 to be part of the replay session, with an associated lead-in screen presented before the digital memory. The illustration of FIG. 10 illustrates a lead-in screen for the last digital memory (in this case, the fifth digital memory) in the replay session at a fourth screen 958 and the fifth digital memory at a fifth screen 960. Progression across the digital memories in the replay session is automatic.

At a sixth screen 962, in some cases, after viewing all the digital memories in the replay session, a dialogue can be presented to the user with text encouraging the user to engage in a 'Moment of Reflection.' The Moment of Reflection is intended to boost the overall meaning of the replay session and increase a depth of processing of each memory.

At a seventh screen 964, in some cases, the user can be presented with usage feedback indicating that number of digital memories created and replayed.

In further cases of the embodiments described herein, the replay session module 172 can determine an optimal time for replay for memory retrieval. In particular, the replay session module 172 determines the optimal time for replay in relation to sleep of the user.

At a neural level, associative learning broadly follows the Hebbian principle: neurons that fire together, wire together. Neural connections are modified via changes in the size and efficacy of synaptic signal transmission, which is made possible by protein synthesis and protein degradation processes that lead to long-term potentiation and long-term depression. This selective strengthening of neural connections leads to consolidation of recent, short-term memories into more stable long-term memories. Learning can be thought of as a hyperexcitable state of the nervous system, where an experiential stimulus can excite, or re-excite, the neurons involved in a prior learning experience. The re-excitation is important to the neural process of consolidation and requires a set amount of time for protein synthesis and degradation. Because of the time this process requires, if one were to reactivate a memory trace during its initial processing (i.e., soon after the event occurred) with a replay session, there would be little memory gain from the replay session. Put differently, if the first replay session occurs very soon after the original event, the memory trace for this original event would already be reactivated and additional reactivation with a replay session would be less effective than if the original memory trace was not already undergoing active processing at the time of initial replay. In addition, sleep is important for memory consolidation, because during sleep the protein synthesis and degradation processes described above are most active. If a memory is reactivated prior to sleep, this memory will be tagged and prioritized for this additional processing during sleep, which will render the memory stronger in the long-term. Thus, the present inventors determined that there are two factors that the system 100 can use to significantly increase the efficacy of the externally-simulated replay session: (1) the proximity of an event's first replay session relative to the original learning event, and (2) the proximity of an event's first replay session relative to sleep. The present inventors determined that if one were to replay an event in close temporal proximity to when that event occurred, there would be a reduced mnemonic benefit of replay, because the event is still activated in the brain. Accordingly, the system 100 advantageously targets replays to occur after protein degradation is complete, but when still in the hyperexcitable state. Thus, initial replays of an event are targeted to be provided prior to sleep, when the memories are still labile. Hence, the memory that was replayed prior to sleep can then undergo protein synthesis during sleep, leading to a longer-lasting trace of that event.

In some cases, the replay session module 172 can abide by a time delay before replaying at block 256, such that replays are only selected at block 254 after a specified delay period has passed. Any suitable delay period can be used. In some cases, the specified delay period can vary based on the length of the actual event. In some cases, the specified delay period is greater than an hour since the digital memory was recorded. In further cases, the specified delay period is greater than 4 hours since the digital memory was recorded.

In some cases, the replay session module 172 can use sleep prediction to determine when to replay at block 256, such that replays are only selected at block 254 during a specified pre-sleep window prior to the user going to sleep on the day the digital memory was recorded. The specified pre-sleep window can be for any suitable duration prior to sleep; for example the specified pre-sleep window can be for the four hours prior to sleep, the three hours prior to sleep, the two hours prior to sleep, or the one hour period prior to sleep. Where the present inventors have determined that a pre-sleep window of two hours is generally most advantageous. In some cases, the sleep timing can be entered beforehand by a user. In other cases, a typical sleep schedule can be entered by the user to allow the replay session module 172 to predict when sleep is to occur. In further cases, the replay session module 172 can use a machine learning model (for example, a regression model) to predict when the user is likely to go to sleep on a certain day based on sleep schedules of previous days, weeks, or years. In some cases, the first replay of a digital memory occurs only during the specified pre-sleep window; where further replays can occur at any time after this first replay. In some cases, the replay session module 172 can use both the specified pre-sleep window and the specified delay period to determine when to first replay a digital memory. In this way, hippocampal replay that generally occurs during sleep can be advantageously enhanced by the replay of the memory in the pre-sleep window, but far enough away from the actual event to allow for protein synthesis.

In some cases, the system 100 can be used to improve memory using spatial navigation. In these cases, the memory creation module 170 can record a sequence of digital memories; for example, at physical locations along a physical route. During replay, the replay session module 172 can replay the sequence of digital memories in order. In this way, the user can benefit from both temporal order memory and allocentric memory for locations encountered along the route, improving both details associated with each physical location and improving spatial navigation. In some cases, other facts or details that may or may not have to do with the physical location can be presented with each digital memory in the sequence; in this way, memorization of facts can be increased with the use of replay of the system 100. While these cases are described for physical locations along a physical route, it is understood that this could be applied, as appropriate, for locations in a virtual world in virtual or mixed reality. In this way, users could travel along novel routes in a virtual environment and subsequently replay their experience with the system 100 to facilitate learning of these routes. In some cases, this can be augmented to include perceptual input from the vestibular and proprioceptive systems by combining a virtual or mixed reality device with a device that approximates self-propelled movement; for example, a treadmill, stationary bicycle, rowing machine, or the like.

The present inventors conducted example experiments to validate at least some of the advantages of embodiments described herein (referred to as "Hippocamera"). In one of the example experiments, participants were asked to record 5 events per day, and engage replay 6 times per day. This experiment was set up such that 50% of all events recorded would be hidden, and the remaining 50% would be replayed. For this experiment, participants used the system 100 for two weeks, were tested on their memory for events recorded at 1-week intervals and completed an fMRI a week later. Participants were invited to return to complete a second memory assessment and fMRI three months later. For this experiment, percent boost of details replayed by the system 100 relative to hidden were determined as:

$$\% \text{ Boost} = \frac{(\text{Replayed} - \text{Hidden})}{\text{Hidden}}$$

Figure 11:
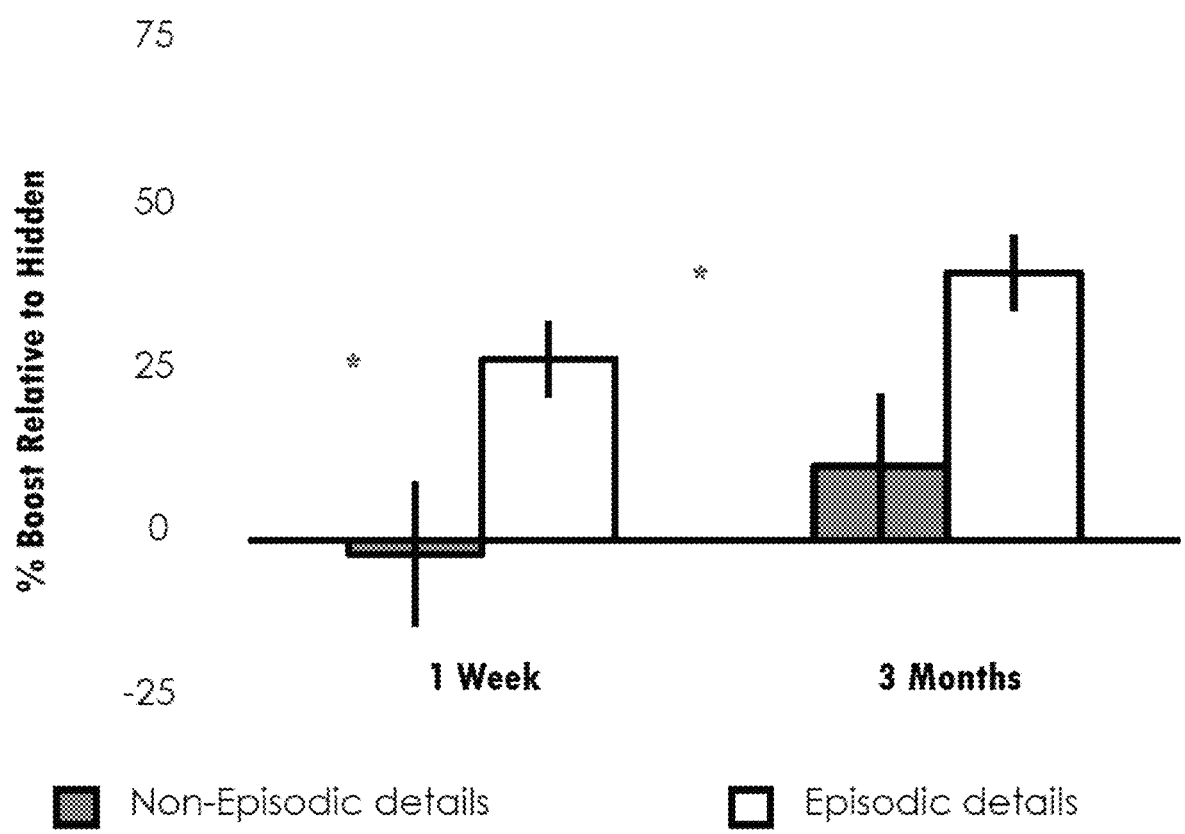
FIG. 11 is a bar chart illustrating results of an example experiment using the system of FIG. 1.
Figure 12:
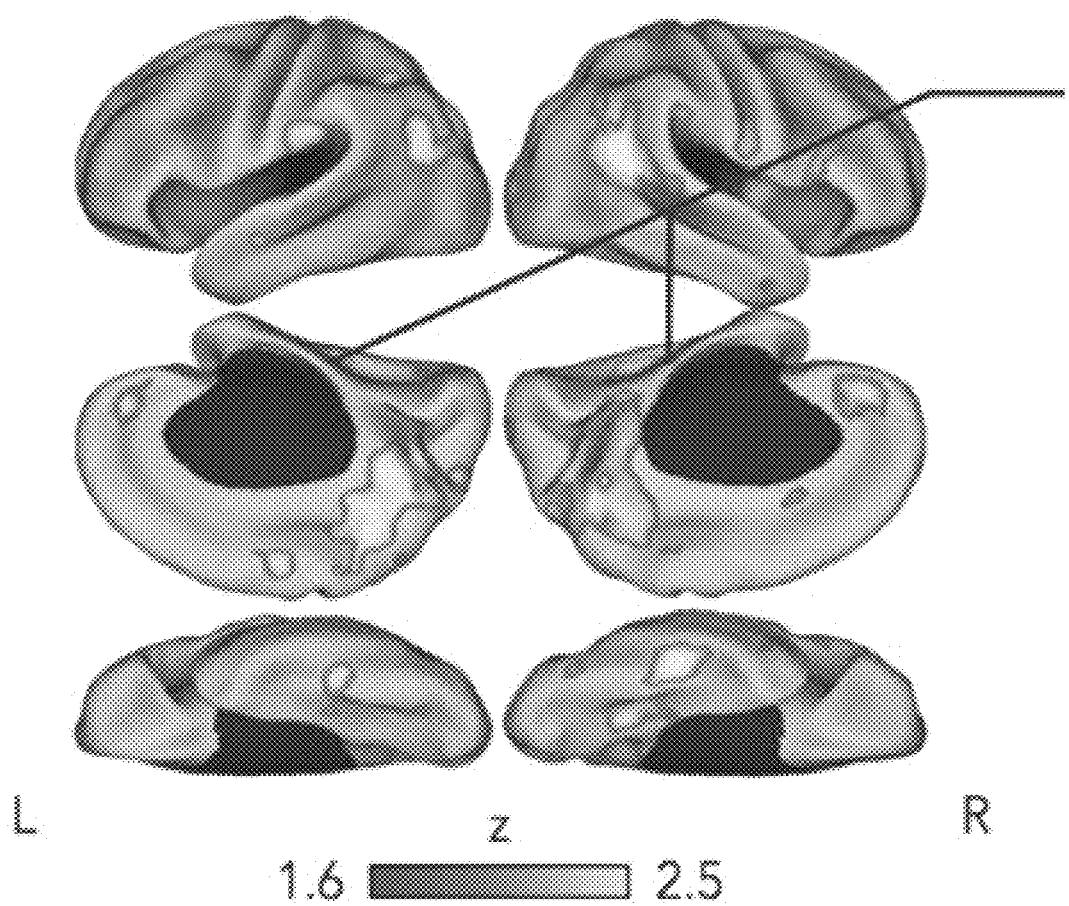
FIG. 12 illustrates an fMRI scan for the example experiment of FIG. 11.

As illustrated in the results chart of FIG. 11, this experiment demonstrated that the system 100 provided robust episodic memory gains, at both original and follow-up testing. As illustrated in in FIG. 12, the fMRI conducted also showed that memory for events replayed with the system 100 was associated with enhanced hippocampal activity reflected in more distinct neural codes. Replay promoted hippocampal distinctiveness (area indicated with lines in FIG. 12) and enhanced the neural representation of events in the autobiographical memory network. This experiment also showed that participants' recollections of replayed events were described in more positive language than hidden events. This suggests that not only is there a richer recollection of the replayed events, but that they are being recalled in a more positive way.

Figure 13:
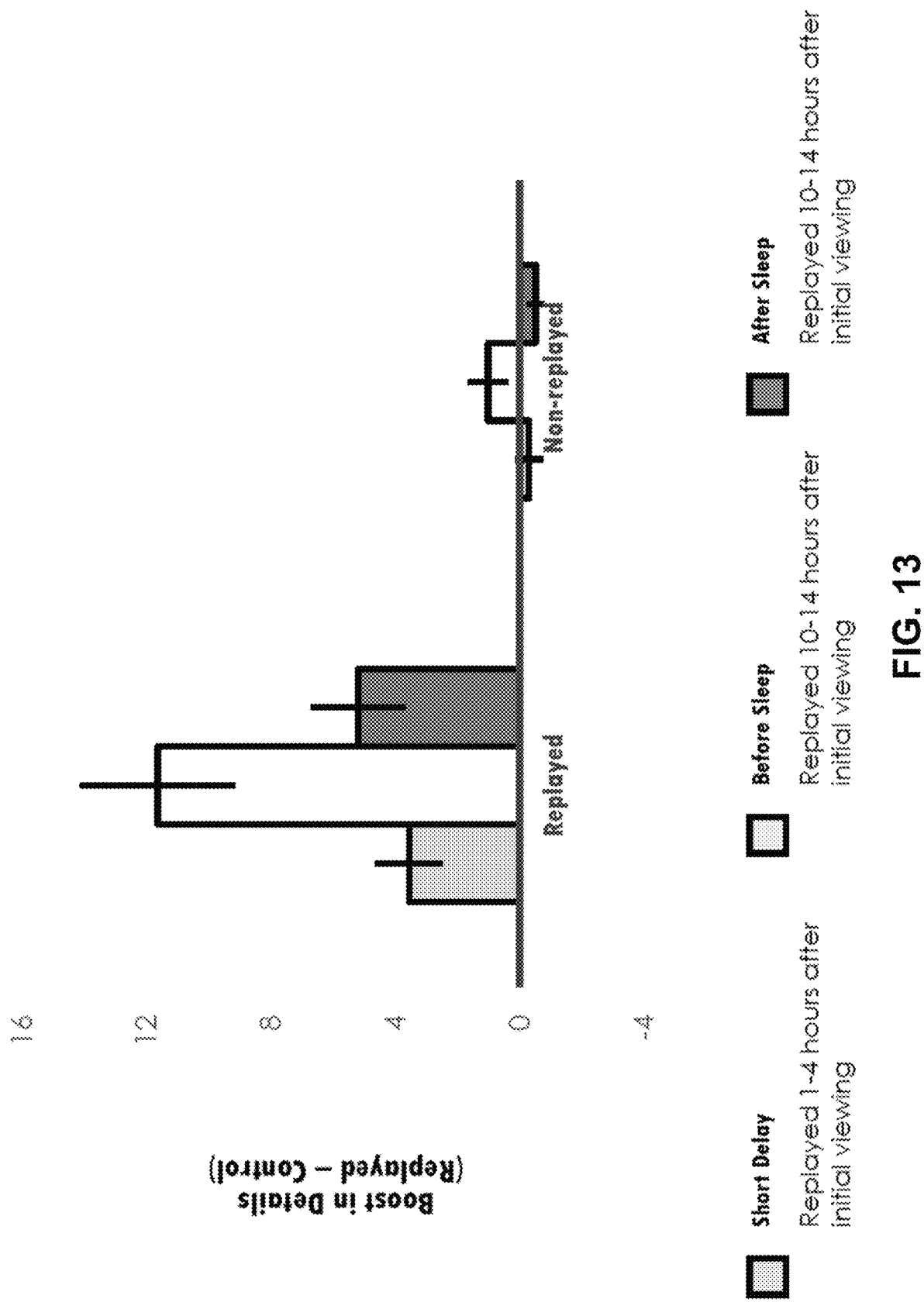
FIG. 13 is a bar chart illustrating results of another example experiment using the system of FIG. 1.

In another example experiment, the present inventors systematically assessed an optimal time of replay, particularly in regard to sleep. A standardized naturalistic stimulus was administered to a number of individuals in a lab. The participants were asked to replay specific scenes of the stimulus using the system 100. Replay protocols were titrated (e.g., frequency, duration, proximity to sleep) to determine the optimal time to replay an event with the system 100. As illustrated in FIG. 13, the results indicated that the best time to replay an event is the same day it occurred, prior to going to sleep, as described in embodiments described herein. This result represents an advantageous way of exploiting protein synthesis of individual memories and memory consolidation that occurs in slow-wave sleep.

Figure 14:
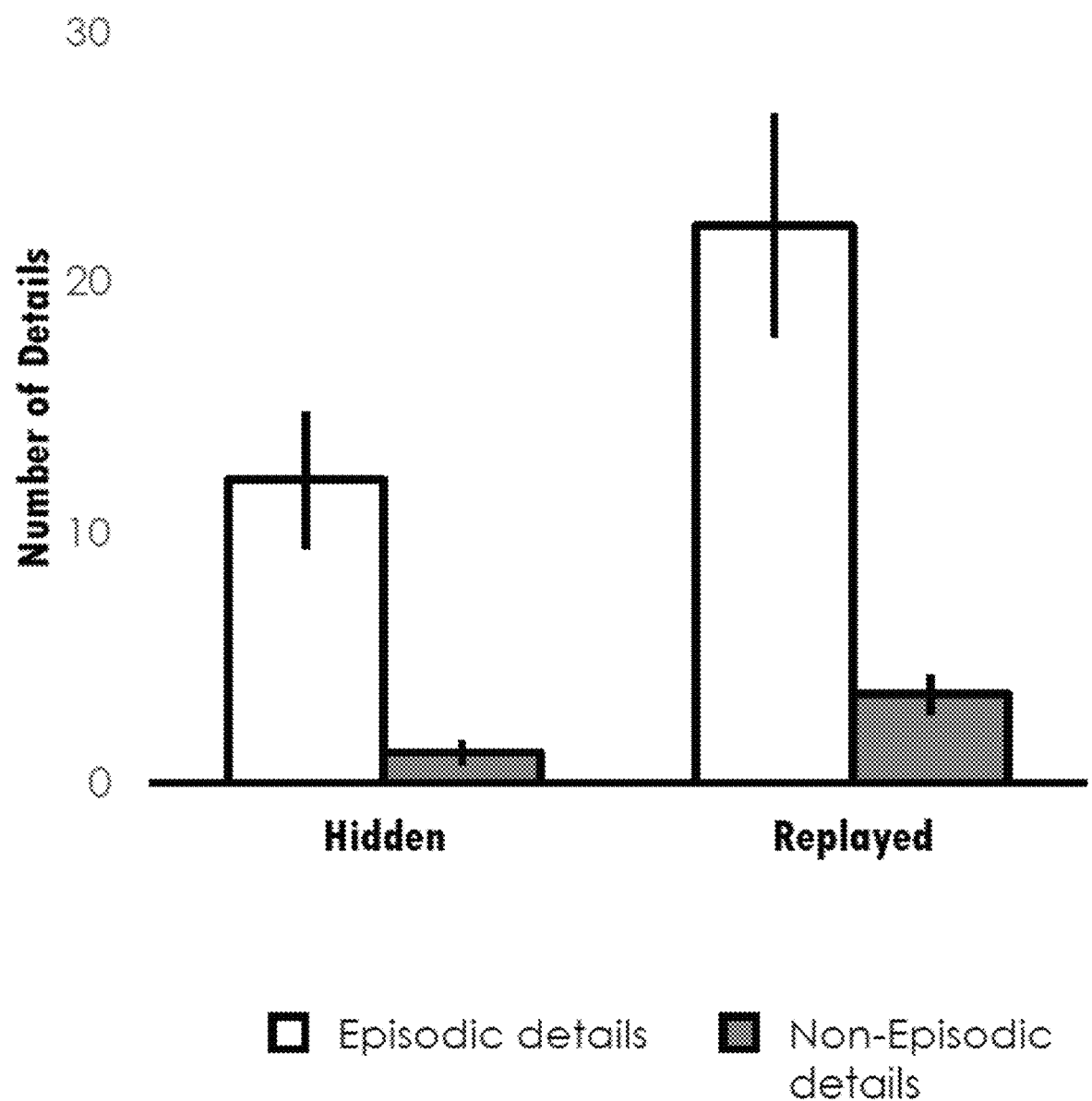
FIG. 14 is a bar chart illustrating results of yet another example experiment using the system of FIG. 1.

In another example experiment, a group of healthy young adults and a second group of healthy older adults used the system 100 for 9 weeks. They were tested on their memory for events recorded using the system 100 after three months, and all completed an fMRI experiment after use. Participants were invited to return to complete a second memory assessment and fMRI experiment three months after use of the system 100. In this experiment, participants had events replayed in the evening, a certain amount of time before going to sleep. As illustrated in FIG. 14, the results found a nearly two-fold increase in the number of episodic details participants described for replayed events, suggesting that there is better event recall with longer usage, and that the time of replay is improving the mnemonic benefit.

Figure 15:
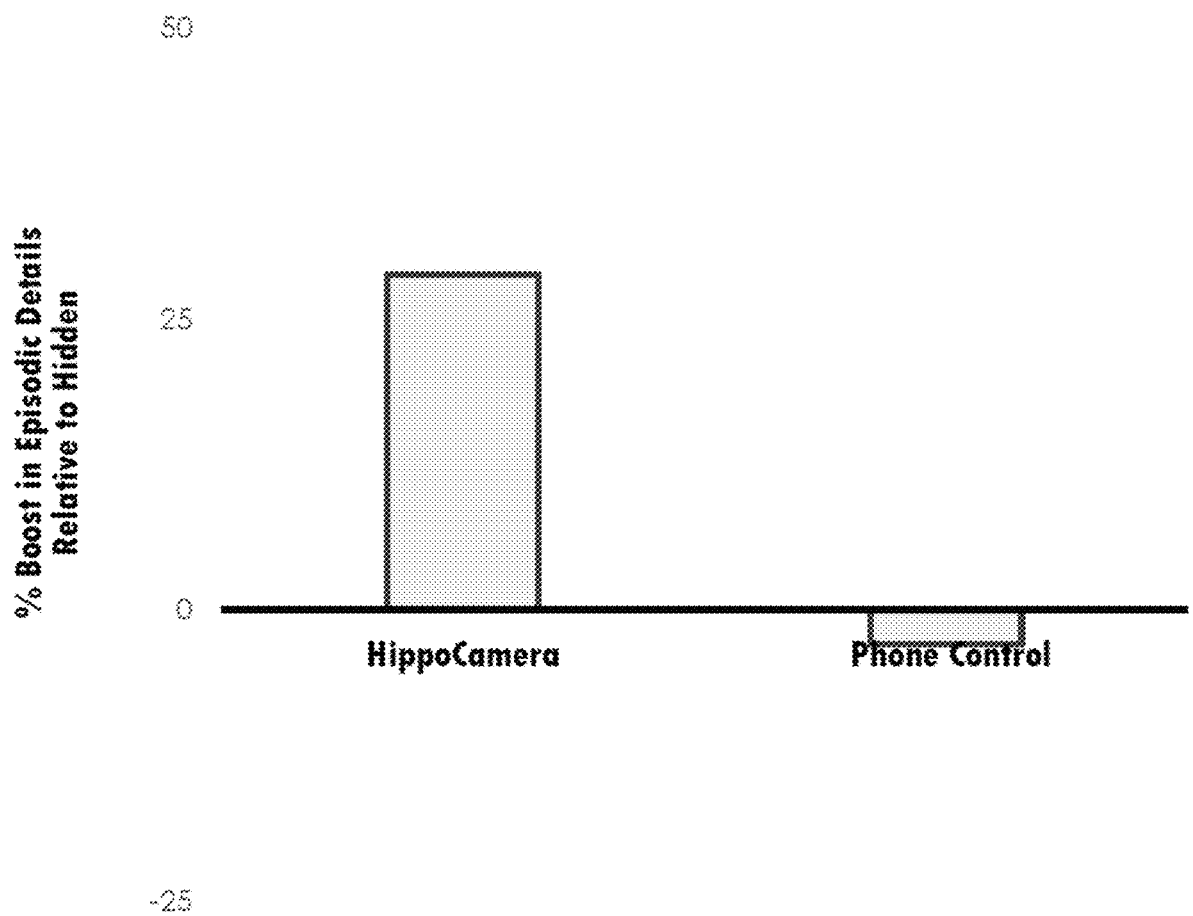
FIG. 15 is a bar chart illustrating results of yet another example experiment using the system of FIG. 1.

In another example experiment, the system 100 was compared against a control. In the Control version, participants were asked to share photos they currently have on their phone from the previous three months. Photos were selected from distinct days, using the picture metadata, that look like they could come from meaningful events. Half of the selected photos were replayed using the system 100 for two weeks, and then participants completed a memory assessment. When comparing the same participants' recollection data of the previous example experiments (hidden trials vs. replayed trials) and the control (hidden trials vs. replayed trials), the results, as illustrated in FIG. 15, indicated that each individual has a replay benefit using the system 100, but generally no benefit for the control. This indicates that simply replaying photographs or videos from one's existing phone does not receive the same mnemonic benefits as using the system 100. For example, due to the fact that participants do not take pictures with the same intentionality as in the recordation of an event using the system, or due to the fact that such pictures do not have the same multimodal cues as an event using the system (e.g., video+audio, including a tagged description).

In another example experiment, the system 100 was tested for its ability to improve memory using spatial navigation, as described herein. Participants learned novel-to-them spatial routes on a guided walking tour of the University of Toronto campus and were later assessed on their memory for the routes they had learned. Each route was designed to have three decision points, where participants would later have to make a navigational judgement to correctly navigate the route. Participants were randomly assigned to one of two conditions, (1) replayed and (2) non-replayed. Participants in the replayed group were asked to use the system 100 to replay digital memories after completing the walking tour. Two days later, all participants were asked to complete a landmark sequencing task to assess temporal order memory, and a vector mapping task to assess allocentric memory.

In contrast to an allocentric representation, an egocentric representation comprises of the spatial relationships between entities in the environment and the self—both an allocentric and egocentric representation of space are thought to be important for successful navigation. To assess egocentric memory for the routes during the guided tour of the above example experiment, participants were presented with images of the start and end locations of a given route simultaneously and asked to verbally describe the route in three cued phases. Participants were first asked to provide the most basic directions to navigate from the probed start location to the probed end location using the route taken during the guided tour. They were then asked to provide a detailed description of their surroundings while traversing the route; participants were told to include descriptions of where elements were in their surroundings in relation to both themselves and other objects. Participants were lastly asked to describe any unique episodic details they recalled from the guided walking tour, including, but not limited to, events that occurred, people they saw, or thoughts they were having during the route. Participants repeated this procedure for each route, with each route being probed in the same order as they were learned during the guided tour. The verbal description of each route was recorded for later transcription and scoring. The verbal descriptions were also given a subjective score on a 1-7 Likert scale as a measure of accuracy. It was determined that participants in the replayed condition had a more accurate and more detailed description of the routes than participants in the non-replayed condition.

Figure 16:
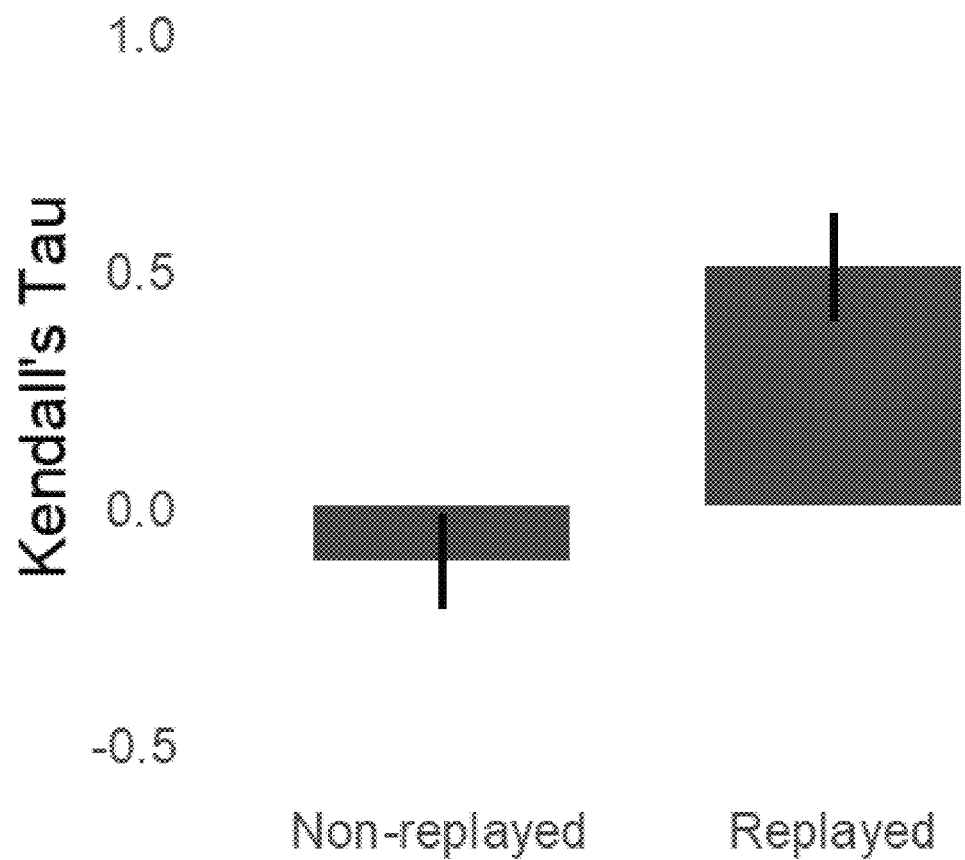
FIG. 16 is a bar chart illustrating results of yet another example experiment using the system of FIG. 1.
Figure 17:
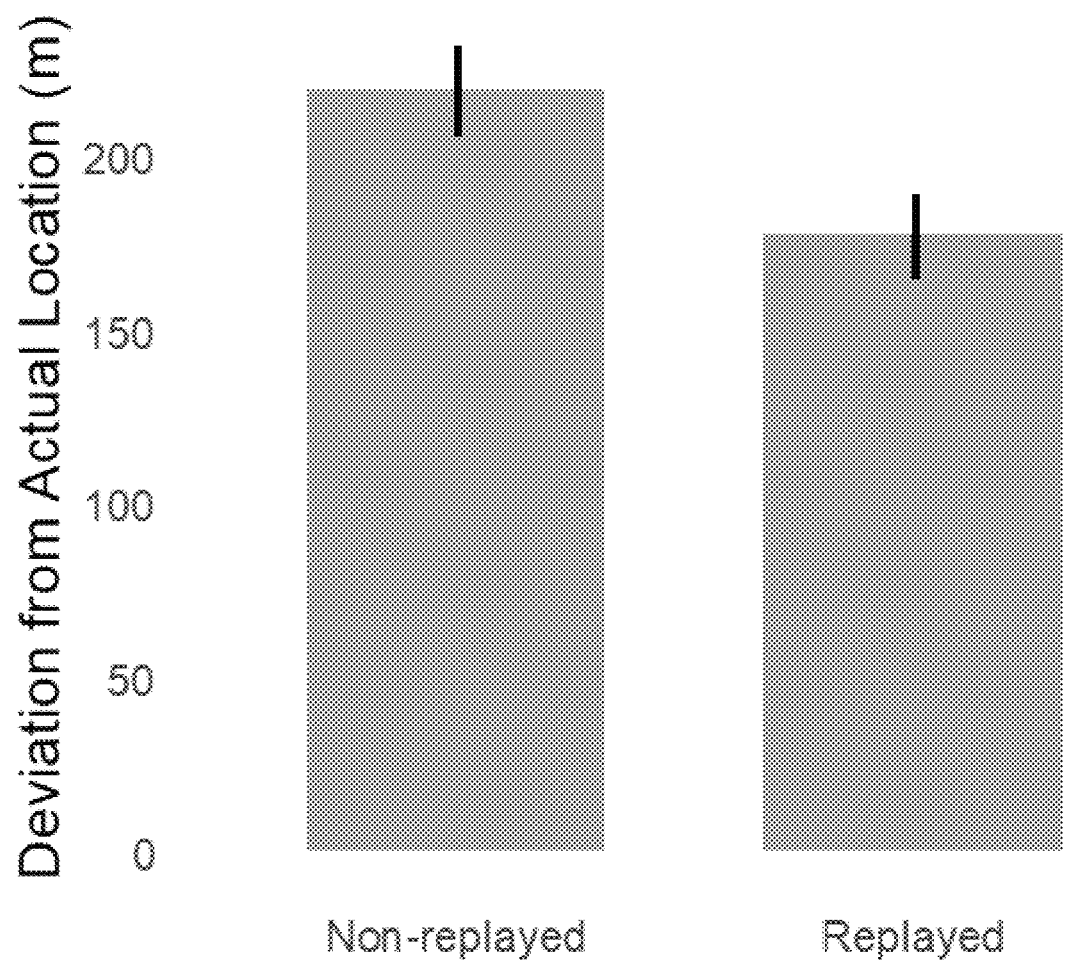
FIG. 17 is a bar chart illustrating further results of the example experiment of FIG. 16.

For the landmark sequencing task, Kendall's tau coefficient was determined between the recalled temporal sequence and the actual temporal sequence. An independent measures t-test showed that participants in the replayed condition had a significantly higher Kendall's tau coefficient than participants in the Non-replayed condition; $t(29)=4.14$, $SE=0.075$, $p=0.00028$ (as illustrated in FIG. 16). For the vector mapping task, the geographical distance between a guessed location and an actual location (deviated distance) was determined using Vincenty's formula. A generalized linear mixed-effects model showed a significant fixed effect of replay condition, $\beta=-0.14$, $SE=0.068$, $t(32)=-2.11$, $p=0.043$, Odds-Ratio=0.87:1; with participants in the replayed condition having a smaller deviated distance than participants in the non-replayed condition (as illustrated in FIG. 17).

Figure 18:
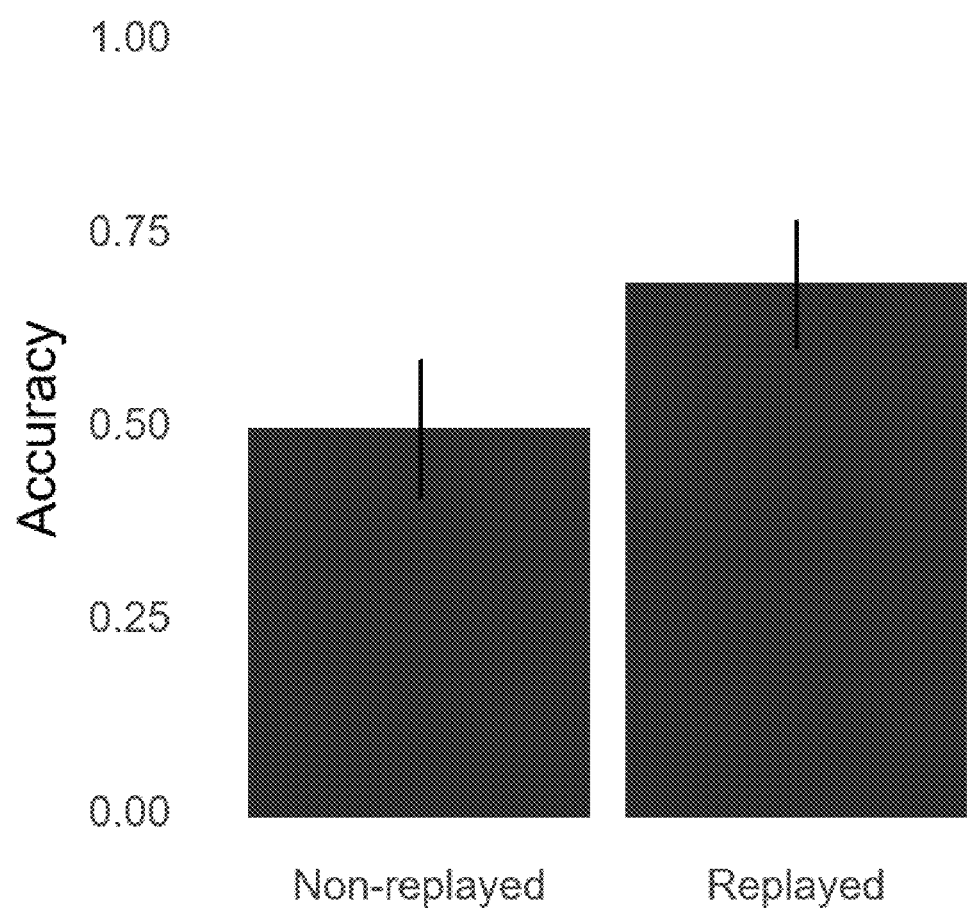
FIG. 18 is a bar chart illustrating results of yet another example experiment using the system of FIG. 1.

In another example experiment, the system 100 was tested for its ability to improve learning of facts or details associated with locations learned during spatial navigation. Participants learned two sets of novel-to-them spatial routes on a guided walking tour of the University of Toronto campus and were later assessed on their memory for the routes they had learned. Each route was designed to have three decision points, where participants would later have to make a navigational judgement to correctly navigate the route. In addition, two facts were learned at points along each route. For each route, participants were randomly assigned to one of two conditions, (1) replayed and (2) non-replayed. Participants in the replayed group were asked to use the system 100 to replay digital memories after completing the walking tour. Participants were then asked to return two days later to assess their memory of the semantic facts learned during the walking tour. Participants were given a multiple-choice style questionnaire with eight questions that corresponded to a detail from each of the semantic facts that were learned during the guided tour. Comparing the same participants' memory for facts learned during the replayed routes compared to those learned during the non-replayed routes, as illustrated in FIG. 18, indicated that 75% of individuals have a replay benefit using the system 100 for memory of facts learned during the guided tour.

In the above two example experiments with spatial memory components, virtual or mixed reality technology can also be used to simulate or enhance spatial navigation. Navigation in real-life and virtual reality have been shown to have comparable subjective ratings on various experiential qualities, suggesting that the system's 100 use of replay would translate into the domain of virtual environments. In this way, users could travel along novel routes in a virtual environment and subsequently replay their experience to facilitate learning of these routes. Although navigation in stationary virtual reality lacks the involvement of perceptual input from our vestibular and proprioceptive systems, this can be mitigated by combining a virtual reality headset with, for example, a treadmill.

The embodiments described herein advantageously include automated notifications that encourage a user to replay digital memories in a distributed manner throughout the course of each day. Also advantageously, a reminder schedule is optimized based on empirical data. The embodiments described herein provide intelligent automation of digital memories that do not rely on the user remembering to view videos, and ensures that memory replay is spaced, rather than massed, for more effective recall. In this way, spacing of replay sessions can provide a connected and coherent trace of daily episodes.

The embodiments described herein also advantageously replay digital memories in a manner that approximates endogenous hippocampal replay; for example, frequency, duration, speed, forward/backward structure, or the like. In this way, a user's memory traces can be strengthened via replay from an external device, in addition to the replay that is produced internally via the hippocampus. Especially in individuals with memory impairments, in whom the structures initiating hippocampal replay may be compromised, the externally mediated replay can produce substantial memory benefits. The embodiments described herein, also advantageously, can prioritize relevant memories for subsequent memory-enhancing hippocampal processing, for example, by providing replay prior to sleep. In this way, the system 100 enhances memory creation over hippocampus behaviour that generally replays only during sleep. In this way, the system 100 goes beyond merely externally mimicking hippocampal replay because providing replay, for example in proximity to sleep, benefits recall by prioritizing memories for additional memory-enhancing processing during sleep or during rest. As such, the replay sessions of the present embodiments do not merely mimic endogenous hippocampal replay, but rather set up the internal representation of a specific memory for enhanced processing during sleep or during rest.

The embodiments described herein also advantageously combine rich, user-generated, multi-sensory information at the time of digital memory creation. In some embodiments, digital memories include, or are supplemented with, "audio tags" that are provided by the user at the time of the original episode. These tags offer a first-person perspective of personally meaningful contextual factors that later allow the user to embed the digital memory into a coherent narrative. In further embodiments, these tags can take other forms, for example, a text description of the event or a video description of the event.

The embodiments described herein also advantageously support automated curation of digital memories in a situationally aware manner. In a healthy brain, memories are typically coherent: one memory leads to another related memory. In this way, embodiments described herein can use machine-learning techniques and machine vision to automatically detect aspects of digital memories which are similar and group them together accordingly for replay sessions. As such, the embodiments described herein can boost memory for single events and reinforce relationships between meaningfully connected memories on the basis of commonalities at, for example, the level of people and the nature of the event.

While some of the present embodiments describe timing of a replay in relation to sleep, it should be understood that sleep includes either a full sleep (such as at night) or a sleep of a shorter duration (such as a nap). For example, a 90-minute nap will generally encompass a full sleep cycle, which includes the phase of slow-wave sleep that is generally important for memory consolidation. Thus, either a nap or a full night's sleep can be used to prioritize replayed events displayed prior to sleep to take advantage of the memory-enhancing processes that happen during slow wave sleep. Additionally, while some of the present embodiments refer to timing with respect to sleep, it should be understood that this can include rest periods that may or may not include sleep; as hippocampal replay may also occur in these rest periods.

Although the foregoing has been described with reference to certain specific embodiments, various modifications thereto will be apparent to those skilled in the art without departing from the spirit and scope of the invention as outlined in the appended claims. The entire disclosures of all references recited above are incorporated herein by reference.

The invention claimed is:

1. A computer-implemented method for digital enhancement of hippocampal replay using a computer, the method comprising:
    creating one or more digital memories, each digital memory created by:
        receiving a tag associated with the digital memory from a user;
        receiving a captured digital memory from the user; and
        associating one or more additional attributes with the digital memory;
    creating a replay session, the replay session comprising one or more digital memories, by:
        associating a target digital memory with the replay session; and
        associating one or more other digital memories with the replay session if such one or more other digital memories meet a measure of commonality with the target digital memory, the measure of commonality at least based on the additional attributes; and
    displaying the replay session to the user within a predetermined period.

2. The method of claim 1, wherein the predetermined period comprises a time delay after capturing of the digital memory.

3. The method of claim 2, wherein the predetermined period is at least four hours.

4. The method of claim 1, wherein the predetermined period comprises a window of time prior to when the user is expected or predicted to go to sleep on the day the digital memory was captured.

5. The method of claim 4, wherein the window of time is less than or equal to two hours in duration.

6. The method of claim 1, wherein creating the one or more digital memories further comprises:
    generating an associative representation with the digital memory, the associative representation comprising at least one of a background colour and a symbol; and
    displaying the associative representation when the respective digital memory is displayed.

7. The method of claim 1, wherein the tag comprises at least one of a recorded audio, a recorded video, and inputted text.

8. The method of claim 1, wherein the captured digital memory comprises at least one of video, an image, audio, and text.

9. The method of claim 1, wherein the additional attributes comprise at least one of a date, a time stamp, location coordinates, replay information, a face recognition score, and an object recognition score.

10. The method of claim 1, wherein the additional attributes comprise at least one of raw video attributes, compressed video attributes, audio tag attributes, and significance rating attributes.

11. The method of claim 1, wherein the additional attributes comprise at least one of date and time stamp attributes, GPS co-ordinates attributes, background colour attributes, icon attributes, and replay information attributes.

12. The method of claim 1, wherein the creating one or more digital memories further comprises assigning a numerical significance rating to each digital memory, the significance rating being classified as a high significance to denote relative importance and a low significance to denote relative unimportance.

13. The method of claim 12, further comprising associating each created digital memory with a queue associated with one of a plurality of bins, and wherein associating the target digital memory with the replay session further comprises selecting a digital memory from a top of the queue from a selected bin.

14. The method of claim 13, wherein each bin has an associated age and importance, and wherein each digital memory is associated with a respective bin based on the age and importance associated with the digital memory.

15. The method of claim 14, wherein selecting the digital memory from the top of the queue from the selected bin comprises:
  selecting the digital memory from a first bin associated with a relatively newer age and higher importance;
  if no digital memory that has not been displayed is present in the queue associated with the first bin, selecting the digital memory from a second bin associated with a relatively newer age and lower importance;
  if no digital memory is present that has not been displayed in the queue associated with the second bin, selecting the digital memory from a third bin associated with a relatively older age and higher importance; and
  if no digital memory is present that has not been displayed in the queue associated with the third bin, selecting the digital memory from a fourth bin associated with a relatively older age and lower importance.

16. The method of claim 1, wherein the captured digital memory comprises a sequence of digital memories associated with a spatial location, and wherein the replay session comprises the sequence of digital memories displayed in sequence.

17. A system for digital enhancement of hippocampal replay, the system comprising one or more processors and a data storage device, the one or more processors configured to execute:
  a memory creation module to create one or more digital memories, each digital memory created by:
    receiving a tag associated with the digital memory from a user;
    receiving a captured digital memory from the user; and
    associating one or more additional attributes with the digital memory;
  a replay session module to create a replay session, the replay session comprising one or more digital memories, by:
    associating a target digital memory with the replay session; and
    associating one or more other digital memories with the replay session if such one or more other digital memories meet a measure of commonality with the target digital memory, the measure of commonality at least based on the additional attributes; and
  a display module to display the replay session to the user within a predetermined period.

18. The system of claim 17, wherein the predetermined period comprises a time delay after capturing of the digital memory.

19. The system of claim 18, wherein the predetermined period is at least four hours.

20. The system of claim 17, wherein the predetermined period comprises a window of time prior to when the user is expected or predicted to go to sleep on the day the digital memory was captured.

21. The system of claim 20, wherein the window of time is less than or equal to two hours in duration.

22. The system of claim 17, wherein creating the one or more digital memories further comprises:
  generating an associative representation with the digital memory, the associative representation comprising at least one of a background colour and a symbol; and
  displaying the associative representation when the respective digital memory is displayed.

23. The system of claim 17, wherein the additional attributes comprise at least one of a date, a time stamp, location coordinates, replay information, a face recognition score, and an object recognition score.

24. The system of claim 17, wherein the additional attributes comprise at least one of raw video attributes, compressed video attributes, audio tag attributes, and significance rating attributes.

25. The system of claim 17, wherein the additional attributes comprise at least one of date and time stamp attributes, GPS co-ordinates attributes, background colour attributes, icon attributes, and replay information attributes.

26. The system of claim 17, wherein the creating one or more digital memories further comprises assigning a numerical significance rating to each digital memory, the significance rating being classified as a high significance to denote relative importance and a low significance to denote relative unimportance.

27. The system of claim 26, the memory creation module further associates each created digital memory with a queue associated with one of a plurality of bins, and wherein associating the target digital memory with the replay session further comprises selecting a digital memory from a top of the queue from a selected bin.

28. The system of claim 27, wherein each bin has an associated age and importance, and wherein each digital memory is associated with a respective bin based on the age and importance associated with the digital memory.

29. The system of claim 28, wherein selecting the digital memory from the top of the queue from the selected bin comprises:
  selecting the digital memory from a first bin associated with a relatively newer age and higher importance;
  if no digital memory that has not been displayed is present in the queue associated with the first bin, selecting the digital memory from a second bin associated with a relatively newer age and lower importance;
  if no digital memory is present that has not been displayed in the queue associated with the second bin, selecting the digital memory from a third bin associated with a relatively older age and higher importance; and if no digital memory is present that has not been displayed in the queue associated with the third bin, selecting the digital memory from a fourth bin associated with a relatively older age and lower importance.

30. The system of claim 17, wherein the captured digital memory comprises a sequence of digital memories associated with a spatial location, and wherein the replay session comprises the sequence of digital memories displayed in sequence.

\* \* \* \* \*